(12) United States Patent
Asada et al.

(10) Patent No.: US 7,641,614 B2
(45) Date of Patent: Jan. 5, 2010

(54) WEARABLE BLOOD PRESSURE SENSOR AND METHOD OF CALIBRATION

(75) Inventors: Haruhiko H. Asada, Lincoln, MA (US); Phillip Shaltis, Newton, MA (US); Devin B. McCombie, Medford, MA (US); Andrew T. Reisner, Newton, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 107 days.

(21) Appl. No.: 11/508,123

(22) Filed: Aug. 22, 2006

(65) Prior Publication Data

US 2007/0055163 A1    Mar. 8, 2007

Related U.S. Application Data

(60) Provisional application No. 60/710,085, filed on Aug. 22, 2005.

(51) Int. Cl.
 *A61B 5/00* (2006.01)
(52) U.S. Cl. ...................... 600/485; 600/500
(58) Field of Classification Search .......... 600/481–507
 See application file for complete search history.

(56) References Cited

U.S. PATENT DOCUMENTS

| | | | | |
|---|---|---|---|---|
| 4,524,777 | A |  | 6/1985 | Kisioka et al. ............... 128/677 |
| 4,846,189 | A | * | 7/1989 | Sun ............................ 600/492 |
| 5,099,853 | A | * | 3/1992 | Uemura et al. .............. 600/492 |
| 5,111,826 | A |  | 5/1992 | Nasiff ......................... 128/672 |
| 5,152,297 | A |  | 10/1992 | Meister et al. .............. 600/485 |
| 5,183,051 | A |  | 2/1993 | Kraidin et al. .............. 600/500 |
| 5,533,511 | A |  | 7/1996 | Kaspari et al. .............. 600/485 |
| 5,778,879 | A |  | 7/1998 | Ota et al. .................... 128/672 |
| 5,995,859 | A |  | 11/1999 | Takahashi ................... 600/323 |

(Continued)

FOREIGN PATENT DOCUMENTS

WO    WO 98/04182    2/1998

(Continued)

OTHER PUBLICATIONS

Asada et al. "Mobile Monitoring with Wearable Photoplethysmographic Biosensors," IEEE Engineering in Medicine and Biology Magazine, vol. 22(3), pp. 28-40, May/Jun. 2003.

(Continued)

*Primary Examiner*—Robert L Nasser
(74) *Attorney, Agent, or Firm*—Sunstein Kann Murphy & Timbers LLP

(57) ABSTRACT

Methods and apparatus for measuring arterial blood pressure at an extremity of a subject. Arterial blood pressure is derived from a circulatory measurement performed on an extremity of a subject and the circulatory measurement is normalized to account for the instantaneous vertical displacement of the extremity. The vertical displacement of the extremity relative to the heart of the subject is obtained using the angular orientation of the subject's extremity. An improved photoplethysmograph can discriminate light traversing the extremity from ambient light on the basis of differential response. The apparatus may have a conducting polymer actuator for applying pressure to the extremity of the subject. A pulsatile waveform from the photoplethysmographic signal may be obtained at a plurality of externally applied pressures to calibrate the photoplethysmograph.

56 Claims, 14 Drawing Sheets

U.S. PATENT DOCUMENTS

| | | | |
|---|---|---|---|
| 6,280,390 B1 | 8/2001 | Akselrod et al. | 600/485 |
| 6,309,359 B1* | 10/2001 | Whitt et al. | 600/485 |
| 6,322,515 B1* | 11/2001 | Goor et al. | 600/485 |
| 6,547,741 B2* | 4/2003 | Mori et al. | 600/490 |
| 6,932,772 B2 | 8/2005 | Kan | 600/490 |
| 7,014,611 B1 | 3/2006 | Geddes et al. | 600/490 |
| 7,214,193 B2* | 5/2007 | Freund et al. | 600/490 |
| 7,238,159 B2* | 7/2007 | Banet et al. | 600/485 |
| 2002/0177781 A1 | 11/2002 | Amano | 600/485 |
| 2002/0188205 A1* | 12/2002 | Mills | 600/481 |
| 2004/0024326 A1* | 2/2004 | Yeo et al. | 600/500 |
| 2004/0162493 A1* | 8/2004 | Mills | 600/481 |
| 2005/0096557 A1 | 5/2005 | Vosburgh et al. | 600/509 |
| 2005/0215912 A1* | 9/2005 | Freund et al. | 600/485 |
| 2006/0074322 A1 | 4/2006 | Nitzan | 600/485 |
| 2006/0195034 A1 | 8/2006 | Skrabal et al. | 600/485 |

FOREIGN PATENT DOCUMENTS

| | | |
|---|---|---|
| WO | WO 98/25511 | 6/1998 |
| WO | WO 03/039326 | 5/2003 |

OTHER PUBLICATIONS

Shaltis et al. "*A Hydrostatic Pressure Approach to Cuffless Blood Pressure Monitoring*," 2004 26th Annual International Conference of the IEEE/EMBS, San Francisco, CA USA, Sep. 1-5, 2004.

Shaltis et al. "*Calibration of the Photoplethysmogram to Arterial Blood Pressure: Capabilities and Limitations for Continuous Pressure Monitoring*," 2005 27th Annual International Conference of the IEEE/EMBS, Shanghai, China, Sep. 1-4, 2005.

Asada et al. "*Towards the Development of Wearable Blood Pressure Sensors: A Photo-Plethysmograph Approach*," Mini-Symposium, 2005 27th Annual International Conference of the IEEE/EMBS, Shanghai, China, Sep. 1-4, 2005.

Shaltis et al. "*Novel Design for a Wearable, Rapidly-Deployable, Wireless Noninvasive Triage Sensor*," 2005 27th Annual International Conference of the IEEE/EMBS, Shanghai, China, Sep. 1-4, 2005.

Reisner et al. "*A Miniaturized Device Capable of Near-Imperceptible Function: Toward a Wearable Monitor for Continuous Arterial Blood Pressure,*" 2006 MGH Scientific Advisory Committee Research Symposium, Feb. 17, 2006.

Shaltis et al. "*Wearable, Cuff-less PPG-Based Blood Pressure Monitor with Novel Height Sensor,*" 2006 28th Annual International Conference of the IEEE/EMBS, New York, New York, Aug. 30-Sep. 3, 2006.

Penaz, J. "*Photoelectric Measurement of Blood Pressure, Volume and Flow in the Finger*," Digest of the $10^{th}$ International Conference on Medical and Biological Engineering, Session 7, p. 104, 1973.

Teng et al. "*Continuous and Noninvasive Estimation of Arterial Blood Pressure Using a Photoplethysmographic Approach,* " Proceedings of the $25^{th}$ Annual International Conference of the IEEE EMBS, pp. 3153-3156, Sep. 17-21, 2003.

Kamakoshi et al. "*Current Developments in non-invasive measurement of arterial blood pressure*," J. Biomed, Eng. vol. 10, pp. 130-137, Apr. 1988.

Kamakoshi et al. "*Long-term ambulatory monitoring of indirect arterial blood pressure using a volume-oscillometric method*," Med. & Biol. Eng. & Comput., vol. 23, pp. 459-465, 1985.

*International Search Report*, dated Jan. 19, 2007; received Jan. 23, 2007; PCT/US2006/032601.

*International Search Report*, dated Apr. 4, 2007; received Apr. 17, 2007; PCT/US2006/045590.

O'Rourke (ed.) "*Properties of the arterial wall: theory*", McDonald's Blood Flow in Arteries: Theoretical Experimental & Clinical Principles, Oxford U. Press, pp. 54-72, 1997.

Allen et al. "*Modelling the relationship between penpheral blood pressure and blood volume pulses using linear and neural network system identification techniques*", Physiological Measurement, 20, pp. 287-301, 1999.

\* cited by examiner $a = 9.8 \text{ m/s}^2$ $a = 9.8 \text{ m/s}^2 \times \cos\theta_1$ $a = 0 \text{ m/s}^2$

WEARABLE BLOOD PRESSURE SENSOR AND METHOD OF CALIBRATION

The present application claims the priority of U.S. Provisional Application Ser. No. 60/710,085, filed Aug. 22, 2005, which application is incorporated herein by reference.

TECHNICAL FIELD

The present invention relates to methods and apparatus for measuring arterial blood pressure (ABP) at an extremity of a subject, and more particularly, to a method for calibrating a photoplethysmogram signal at an extremity of a subject.

BACKGROUND OF INVENTION

Accurately measured arterial blood pressure (ABP) is one of the most critical vital signs available for both the diagnosis and the treatment of patients. An elevated ABP, for example, left untreated, may lead to a variety of cardiovascular diseases, and, as shown by Amery et al., *Mortality and Morbidity Results from the European Working Party on High Blood Pressure in the Elderly Trial (EWPHE)*, Lancet, pp. 1349-54 (1985), to a significant decrease in life expectancy. Conversely, overestimation of ABP can lead to exposure to potential side effects from medications as well as unnecessary changes in both a patient's diet and lifestyle.

It has been recognized that ambulatory blood pressure monitoring by means of wearable sensors has the potential to enable new levels of health-related vigilance and medical care in a number of novel settings. Benefits may be realized in applications ranging from the improved diagnosis and treatment of a number of major diseases or even cardiovascular catastrophes which could occur for a wide range of patients.

Wearable blood pressure monitoring (WBPM) solutions, in various stages of technologic maturity, exist for gathering basic cardiovascular information. The Portapres® is a finger-based modality which employs the volume-clamp technique, originally developed by Penaz, to provide a continuous ABP waveform. Although it is slightly less-obtrusive than more traditional cuff-based oscillometric methods, the bulky high-bandwidth actuator that it requires is impractical for long-term patient monitoring. Other means for measuring ABP, such as pulse transit time (PTT) and the second-derivative of the photoplethysmograph (PPG), are currently at the research stage of development. These methods typically require additional information from other sensors, such as an electrocardiogram (ECG), and may be prone to motion artifact issues.

Another complication that wearable blood pressure monitors must overcome is the change in blood pressure when the patient shifts the measurement point relative to the heart. The wearable blood pressure sensor disclosed by Yamakoshi et al., *Long-Term Ambulatory Monitoring of Indirect Arterial Blood Pressure Using a Volume-Oscillometric Method*, Med. & Biol. Eng. & Comput., 23, pp. 459-465 (1985), indirectly accounts for the change in blood pressure by monitoring pressure in a fluid filled tube stretching from the cuff to the patient's breast pocket.

Wearable biosensors (WBS), such as the ring sensors described by Rhee et al., *Artifact-Resistant, Power-Efficient Design of Finger-Ring Plethysmographic Sensors*, IEEE Transactions on Biomedical Engineering, vol. 48(7), pp. 795-805, (2001), and by Shaltis et al., *Artifact Resistant, Power Efficient, High Speed Modulation Design for Photo Plethysmographic Ring Sensors*, Annals of Biomedical Engineering, Vol. 29, Supplement 1, (S-117), (2001), both of which publications are incorporated herein by reference, permit continuous cardiovascular (CV) monitoring in a number of novel settings.

Important health benefits such as improved disease tracking and treatment are afforded from noninvasive and unobtrusive sensor assemblies capable of monitoring blood flow, pulse rate, and blood pressure, among other parameters. However, since WBS devices are to be worn without direct doctor supervision, they must be simple to use, comfortable to wear for long periods of time, and reliable under a myriad of changing environmental conditions.

A challenge unique to WBS design is the tradeoff between patient comfort, or long-term wearability, and reliable sensor attachment. Motion-based artifacts are currently one of the most significant factors limiting the acceptance of wearable biosensors. Inflatable cuffs have shown promise for both measuring arterial blood pressure and secure sensor attachments, but are known to significantly interfere with normal blood perfusion and are therefore somewhat limited in their applicability.

SUMMARY OF INVENTION

In accordance with preferred embodiments of the present invention, a method is provided for performing a circulatory measurement on an extremity of a subject. The method has steps of measuring a plethysmographic signal of a plethysmographic sensor disposed on the extremity of the subject at a plurality of heights of the sensor, relative to the heart of the subject, and at an externally applied pressure having a value; and deriving a feature obtainable from a continuous arterial blood pressure waveform from the value of externally applied pressure and the height at which a peak plethysmographic signal is obtained.

In accordance with other embodiments of the invention, the method may have additional steps of modeling the relationship of a derived arterial pressure to the plethysmographic signal by fitting parameters of a specified functional relationship, or, more particularly, modeling the relationship of a derived mean arterial pressure to the peak plethysmographic signal by fitting parameters of a specified functional relationship.

The plethysmographic signal may be a photoplethysmographic signal, and the external pressure may be applied by means of an inflatable cuff or by means of a band using a polymer actuator, or a sensor holder with a protrusion. Measurement of a plurality of heights of the sensor may be derived from at least one angular displacement of the extremity, with an angular displacement of the extremity obtained by means of an accelerometer.

In accordance with further embodiments of the invention, spurious data points may be removed from the plethysmographic signal.

In accordance with other aspects of the invention, a blood pressure measurement device is provided of the type having a plethysmographic sensor disposed on an extremity of a subject capable of sensing a plurality of plethysmographic signals at a plurality of heights of the sensor relative to the heart of the subject, and at an externally applied pressure characterized by a value (that may be zero). The blood pressure measurement device has a processor that receives the plethysmographic signals from the sensor and derives an arterial pressure from the value of externally applied pressure and the height at which a peak plethysmographic signal is obtained.

In accordance with another aspects of the invention, methods are provided for deriving arterial blood pressure from a circulatory measurement performed on an extremity of a subject. These methods have steps of calibrating the circulatory measurement as a function of vertical displacement of the extremity relative to the heart of the subject;

acquiring a measurement of an instantaneous vertical displacement of the extremity of the subject concurrent with the circulatory measurement; and normalizing the circulatory measurement to account for the instantaneous vertical displacement of the extremity.

A method for measuring a height of a position on one or more segments of an extremity of a subject relative to the heart of the subject is provided in other embodiments of the invention. This method has steps of:

measuring acceleration due to gravity at a point on the extremity of a subject; and inferring a height based at least upon the acceleration due to gravity at a point on the extremity of a subject and a temporal criterion.

Other embodiments of the invention provide an improved photoplethysmograph of the type including a light source for illuminating a blood vessel of a subject, where the improvement has an array of photodetectors for detecting light from the light source traversing the blood vessel, and a processor for discriminating light traversing the blood vessel from ambient light changes on the basis of differential response of the array of photodetectors to variations in vessel volume versus their response to changes in ambient light.

In accordance with yet further embodiments of the invention, a device is provided for modulating external pressure applied to an extremity of a subject, wherein the device has at least one conducting polymer actuator for modulating an external pressure applied to the extremity, a pressure sensor for sensing the pressure applied to the extremity; and a processor for receiving signals from the pressure sensor and controlling signal properties sent to the conducting polymer actuator.

Another embodiment of the invention has a method for registering of a photoplethysmograph for optimizing response, having steps of:

illuminating an extremity of a subject with a light source at a plurality of externally applied pressures;

modifying the drive characteristics of the light source at each externally applied pressure;

detecting the light that has traversed the extremity at a detector and generating a plethysmographic signal corresponding thereto; and determining a maximum amplitude pulsatile waveform from the photoplethysmographic signal at each externally applied pressure.

Another aspect of the current invention provides a method for performing a circulatory measurement on a subject. The method has steps of calibrating a plethysmographic signal of a plethysmographic sensor disposed on the subject so as to obtain a mapping of plethysmographic signal to arterial pressure, and then deriving a feature obtainable from a continuous arterial blood pressure on the basis of a measured plethysmographic signal. The step of calibrating, which may be performed using any means, includes measuring a plethysmographic signal at a plurality of elevations of the extremity with respect to the heart of the subject. The method may also entail a step of updating the mapping of plethysmographic signal to arterial pressure on the basis of a partial to complete recalibration.

In yet further embodiments of the invention, a method is provided for applying a knowable pressure at a wall of an artery while detecting differential volumetric pulsations of the artery. In accordance with the method, a pressure is applied to tissue of the subject with a solid protuberance while volumetric pulsations are detected with an optical sensor.

BRIEF DESCRIPTION OF THE DRAWINGS

The invention will more readily be understood by reference to the following description taken with the accompanying drawings in which.

DETAILED DESCRIPTION OF PREFERRED EMBODIMENTS

Figure 1:
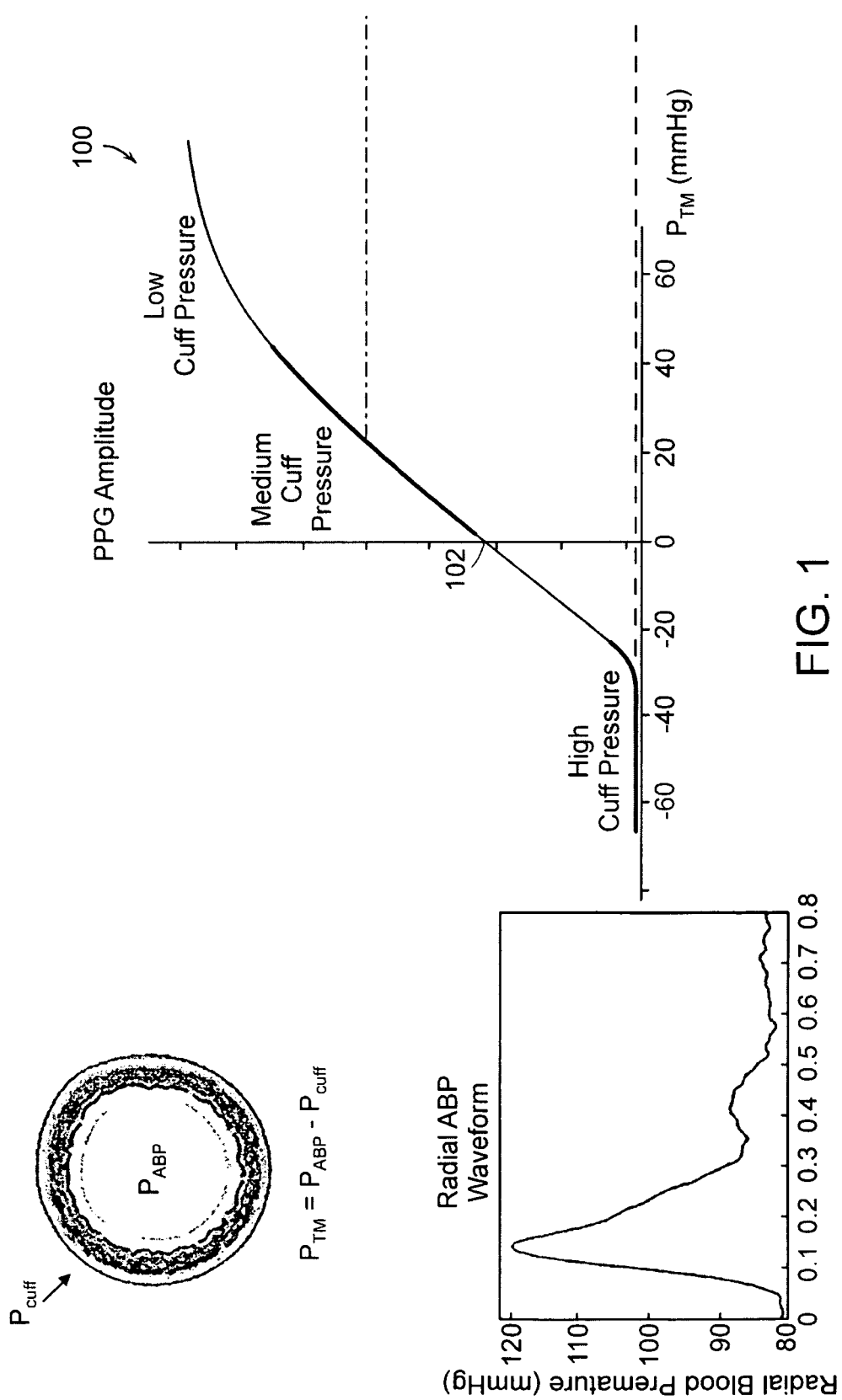
FIG. 1 depicts a sigmoidal compliance curve relating the ABP to the measured PPG waveform.

Advantages of the present invention and its several improvements will be seen when the following detailed description is read in conjunction with the attached drawings. These drawings are intended to provide a better understanding of the present invention, but they are in no way intended to limit the scope of the invention.

Methods and apparatus in accordance with embodiments of the present invention may provide both calibration and measurement and assure accuracy under a diverse range of hemodynamic conditions. A PPG-based signal may be combined with a hydrostatic pressure reference for absolute sensor calibration without the need for a bulky pressure cuff.

As described in detail below, a novel hydrostatic pressure reference method provides for measurement of the height of the heart relative to the sensor unit. A new method and an apparatus for estimating the vertical distance between the heart and the sensor unit are then presented. Application of the height sensor described herein is not limited to use in conjunction with a PPG-based sensor, but may also be used for conventional pulse oscillometric sensors, for example, where the hydrostatic pressure is one of the major sources of measurement error.

Methods in accordance with embodiments of the present invention may advantageously provide for long-term ambulatory measurement of arterial blood pressure (ABP) for the home and field use, and provide for attachment of the sensor by average patients without supervision of clinicians. To guarantee consistent reading and stable attachment to the patient body, a novel automatic sensor registration method and an apparatus are presented. Furthermore, to accommodate the sensor pressure and obtain repeatable measurements, new designs of a micro band using conducting polymer actuators are provided in accordance with certain of the embodiments described.

A sensor unit in accordance with embodiments of the present invention may advantageously enhance the performance of WBS devices. Also, the sensor unit may be used in conjunction with conventional oscillometric devices, or a devises based on the volume clamp method, or any blood pressure sensor measurement performed at a location in which hydrostatic pressure causes an offset relative to the arterial blood pressure at the heart. The sensor assembly may advantageously control localized pressure while maintaining secure sensor contact under a variety of conditions.

Several aspects of the present invention are now addressed: 1) A calibration algorithm for relating photoplethysmogram (PPG) signals to arterial blood pressure[1] (ABP); 2) a method for estimating the mean arterial pressure (MAP) and/or the continuous arterial blood pressure based upon the PPG-ABP calibration curve; 3) a method and apparatus for measuring the height of the sensor relative to the height of the heart; 4) an apparatus for securing a photoplethysmogram sensor unit to the skin and of applying localized pressurization by means of an actuated protuberance; 5) a cuff mechanism using conducting polymer actuators for improving and stabilizing sensor measurements obtained along the length of a wearer's digit; and 6) a method for ascertaining whether the PPG-ABP calibration curve is still serviceable and accurate and a method for estimating changes in the calibration curve that minimizes the needed for recalibrations and maximizes the accuracy of MAP/ABP estimations. Sensors provided in accordance with various embodiments of the present invention may thus advantageously provide noninvasive, compact, and wearable, long-term and continuous monitoring of blood pressure and pressure waveform.

A plethysmogram (PG) is a non-invasive circulatory signal related to the pulsatile volume of blood in tissue. A photoplethysmogram (PPG) is a non-invasive circulatory signal related to the pulsatile volume of blood in tissue, which is derived from a light source.

As used herein, and unless otherwise dictated by context, a "cuff" is to be understood as any device which is capable of applying an external pressure to an extremity.

Instrumentation for monitoring the PPG is found widely in clinical settings in the form of pulse-oximetry probes. Although various factors, including the light source, sensor location, external pressure, and underlying physiological state of the subject, all contribute to the observed PPG waveform, a PPG signal is, to a first approximation, a function of a tissue's pulsatile volumetric changes, which is highly coupled to the underlying ABP waveform.

As shown by Ando et al., *Pressure-Volume Relationships of Finger Arteries in Healthy Subjects and Patients with Coronary Atherosclerosis Measured Non-Invasively by Photoelectric Plethysmography*. 55 Japan Circ. J., pp. 567-75, (1991), as well as by Langewouters et al., *The Static Elastic Properties of 45 Human Thoracic and 20 Abdominal Aortas in Vitro and the Parameters of a New Model*, 17 J. Biomech., pp. 425-35, (1984), these volumetric changes are related to the patient's ABP through a nonlinear compliance relationship. Both the Ando and Langewouters references are incorporated herein by reference.

Maximum compliance occurs when transmural pressure ($P_{TM}$), the pressure difference across a vascular wall, is kept near zero. The transmural pressure is defined as follows:

$$P_{TM} = P_{ABP} \pm P_{height} - P_{cuff} \quad (1)$$

where ($P_{ABP}$) is the internal pressure, ($P_{height}$) is the external hydrostatic pressure, $P_{height} = -\rho \cdot g \cdot h$, ($\rho$ is the density of the blood, g is the acceleration of gravity, and h is the height offset of the measurement site relative to the proximal aorta), and ($P_{cuff}$) consists of any additional externally applied pressure.

For a given pressure change, the volume change, and consequently the PPG amplitude, will be maximum when the transmural pressure is kept near zero. This is illustrated in FIG. 1 as has been confirmed in the research of the present inventors who have developed an effective algorithm for identifying this curve in real time in accordance with the present invention.

The sigmoid-shaped compliance curve 100 demonstrates how the PPG output is a function of the pressure difference across a vascular wall, the transmural pressure ($P_{TM}$). Note that the slope of the sigmoid-shaped compliance curve 100 is maximal near zero transmural pressure ($P_{TM}$) 102. This relationship is the basis for measuring the mean arterial pressure with an external pressure applied by a cuff. At maximum compliance, the known external pressure applied by the cuff is equal to the ABP. Thus, with a PPG sensor and the cuff, the ABP can be found by changing the external pressure applied to the extremity and locating the maximum PPG amplitude. Similarly, the compliance curve can be identified by applying a constant external pressure and varying the applied hydrostatic pressure. The ABP at the extremity can be assumed to change proportionally to the change in height. The height at which the PPG signal is maximum is the height where the artery is at maximum compliance. At this height, the ABP at heart level can be found by adding the hydrostatic pressure and the constant pressure applied by the cuff.

1) Photoplethysmogram Calibration for ABP Measurement

The measurement of ABP should be performed in as comfortable, and as nearly imperceptible, a manner as possible in order to allow the sensor of the present invention and other sensors to be truly "wearable." To achieve this goal, calibration of ABP as a function of PPG amplitude, also referred to as derivation of a PPG-ABP calibration curve, must be performed strategically and in accordance with the following discussion.

A basic PPG-ABP measurement, as well as a calibration for subsequent measurements, may be performed as now described. A known external pressure is applied to a PPG sensor unit and the applied hydrostatic pressure is varied ($P_{height}$), such that the compliance curve illustrated in FIG. 1 may be determined and calibrated, making it possible to provide a continuous ABP estimate with low external cuff pressures. An outline of the procedure involved for this purpose is provided below.

Figure 2:
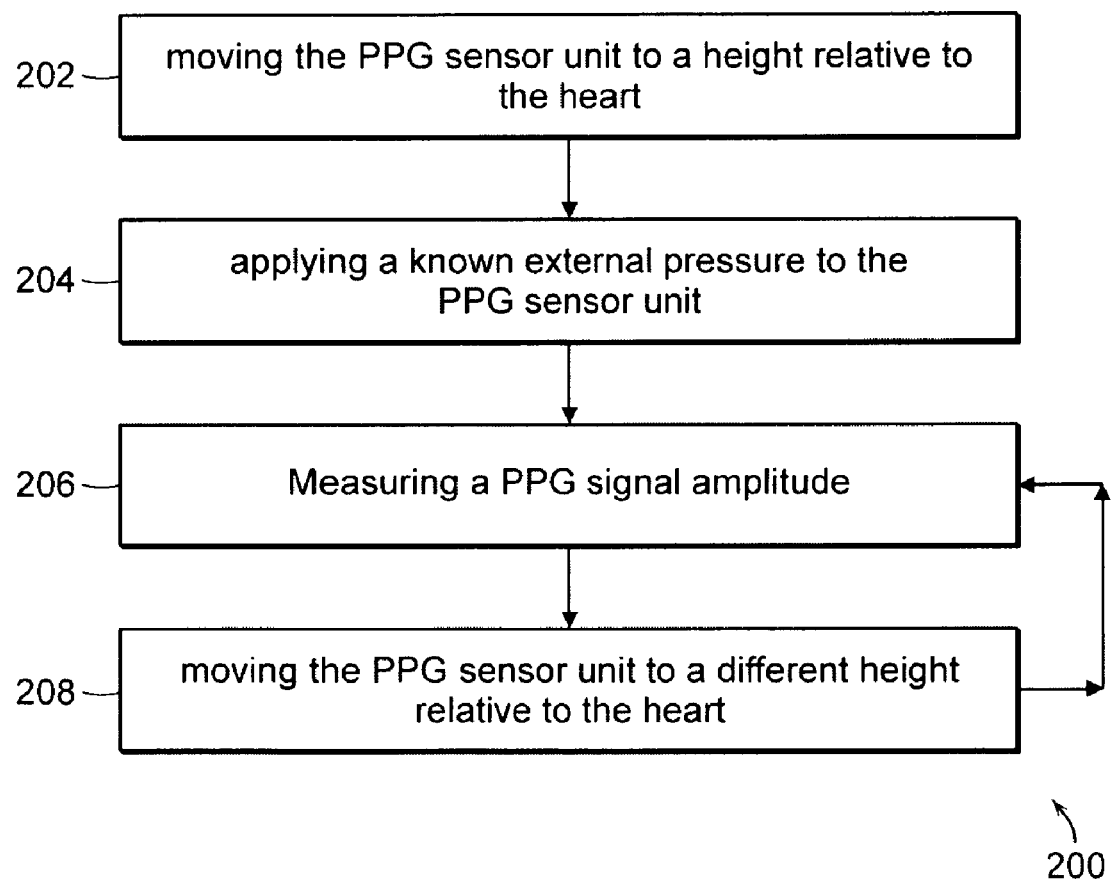
FIG. 2 depicts a block diagram for a method of calibrating an arterial blood pressure measurement, in accordance with an embodiment of the present invention.

After initial attachment of the sensor unit to the patient's finger base, by the patient or by a caregiver, the PPG is adjusted to locate the optimal signal (as will be discussed in more detail in Sec. 3). After the optimal signal has been obtained the PPG signal can be calibrated using a hydrostatic-based oscillometric calibration method 200, as now described with reference to FIG. 2.

Figure 3:
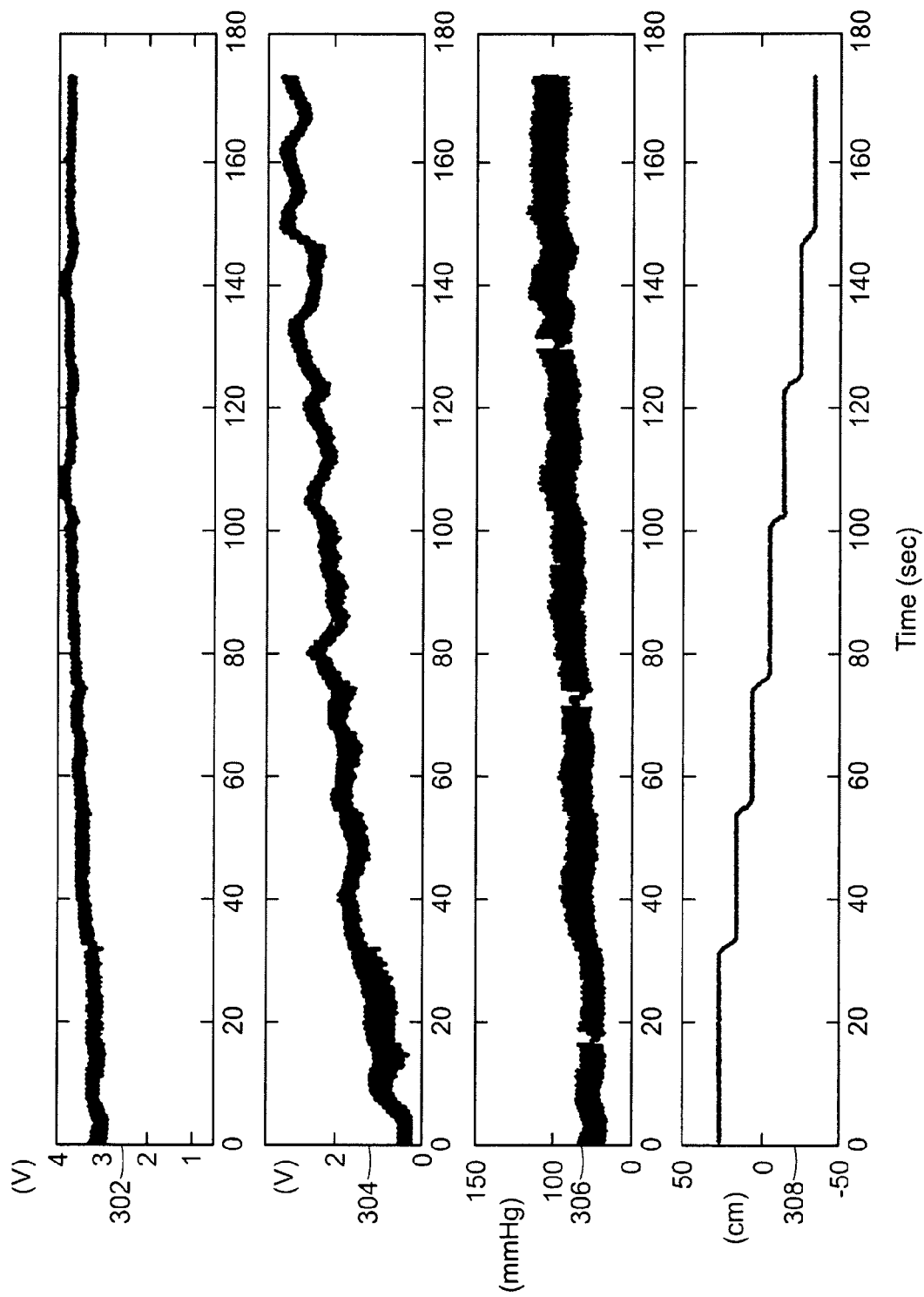
FIG. 3 depicts a plot of the fingerbase PPG output, a plot of the fingertip PPG output, a plot of the fingerbase digital blood pressure, and a plot of measured arm height during a typical 20 second/height experiment, in accordance with an embodiment of the invention.

The wearer's arm and sensor unit are raised to a maximum comfortable height above the heart 202 (typically this is a height of nearly 30 cm above the heart). A known external pressure is applied to the sensor unit ($P_{cuff}$) 204. The PPG signal amplitude at the known externally applied pressure is measured 206. After an initial rest period of approximately two minutes, the arm height is decreased from 30 cm above the heart to 30 cm below the heart in decrements of 10 cm with a rest period of 20 seconds between each height change 208. A typical plot demonstrating the outputs of the fingerbase PPG sensor 302, fingertip PPG sensor 304, digital blood pressure sensor 306, and arm height relative to heart 308 is provided in FIG. 3.

PPG amplitude measurements are obtained by applying a peak detection algorithm to each calibration data set. Once the beat-by-beat amplitudes are calculated, spurious data points are removed by applying a 3-element moving window median filter to the data. The PPG/ABP relationship is complicated by oscillations such as rhythmic variations in microcirculatory blood volume. A moving window averaging is performed to eliminate oscillations between several beats, but other signal processing alternatives exist, including bandpass filtering or fitting a spline, as methods of removing PPG baseline oscillations that are not directly due to oscillations in the ABP, and any such signal processing is within the scope of the present invention.

Then, PPG calibration can be accomplished by combining data from the recorded height sensor ($P_{height}$), cuff pressure sensor ($P_{cuff}$), and amplitude data ($\bar{y}_{AC\_PPG}$), according to Eqns. 2 and 3. Let $\bar{y}_{AC\_PPG}$ be the amplitude of a PPG signal, which varies as the arm is raised, that is, as the height h varies. Assuming that the PPG amplitude takes a maximum within the reach of the arm, the sensor height associated with the maximum PPG amplitude is determined as $$h_{zero\_Ptm} = \arg\max_{h}[\bar{y}_{AC\_PPG}] \quad (2)$$

Using this height of zero transmural pressure, the mean arterial pressure $P_{MAP}$ is given by $$P_{MAP} \cong \rho \cdot g \cdot h_{zero\_Ptm} + P_{cuff} \quad (3)$$

where $P_{cuff}$ is the relatively low pressure applied to the palpable artery as previously noted.

Consequently, it is possible to estimate the internal mean arterial pressure (MAP) by finding, for a given cuff pressure, the height at which the amplitude of the PPG signal is a maximum. Once a MAP has been determined, and assuming that the monitoring conditions remain unchanged, it is then possible to continuously estimate the MAP as a function of time, MAP(t), or more generally, ABP(t) for all $Y_{AC\_PPG}$ (t).

A non-linear calibration curve based upon a best fit of the MAP to the coefficients, $\theta_1$, $\theta_2$, and $\theta_3$, of a Gaussian function of the form, $$\hat{\bar{y}}_{AC\_PPG} = \theta_1 e\left[-\left(\frac{P_r - \theta_2}{\theta_3}\right)^2\right] \quad (4)$$

where $P_r$ is the applied reference pressure, $$P_r = \rho \cdot g \cdot h + P_{ext}; \hat{\bar{y}}_{AC\_PPG}$$

is the estimate of the PPG AC amplitude predicted by the Gaussian model was generated from an initial training set of data. It is to be understood that a fit of mean arterial pressure to other functions of PPG amplitude are within the scope of the present invention.

Figure 4A:
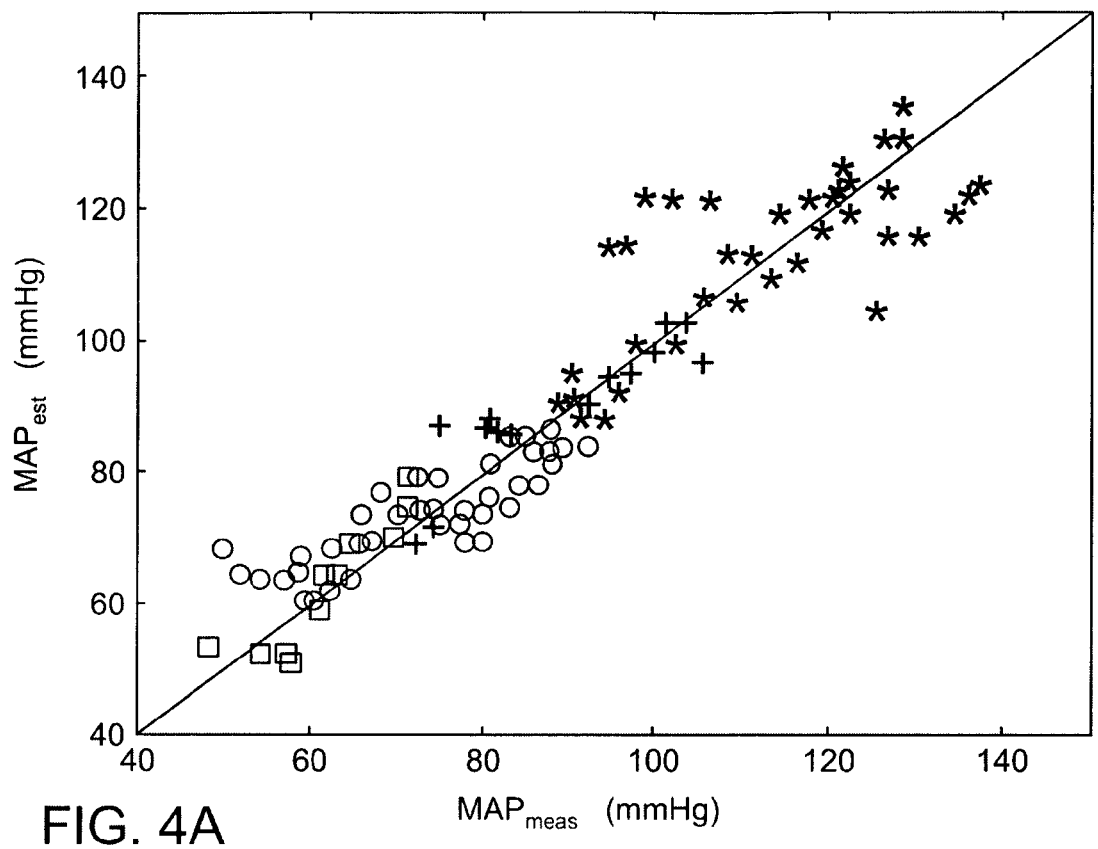
FIG. 4(a) is a plot of estimated PPG-based MAP vs. measured Finapres® MAP for four subjects.

A calibration curve of PPG versus relative change in $P_{TM}$, which is modified by the change in height, is obtained with the y-intercept (that is to say, at zero transmural pressure) identified where the slope of PPG-versus-$P_{TM}$ is maximum[2]. This is the same principle which underlies oscillometry BP measurement. Subsequently, the $P_{TM}$ can be readily estimated from the PPG, using the calibration curve. Since external pressure is directly measured, ABP can be computed: $P_{TM}$ minus the external pressure. In tests performed on the system, an excellent agreement was found between the calibrated PPG signal and a measured Finapres® MAP for calibrations performed in 20 seconds, with 95% limits of agreement at ±16.4 mmHg, as plotted in FIG. 4.

Figure 4B:
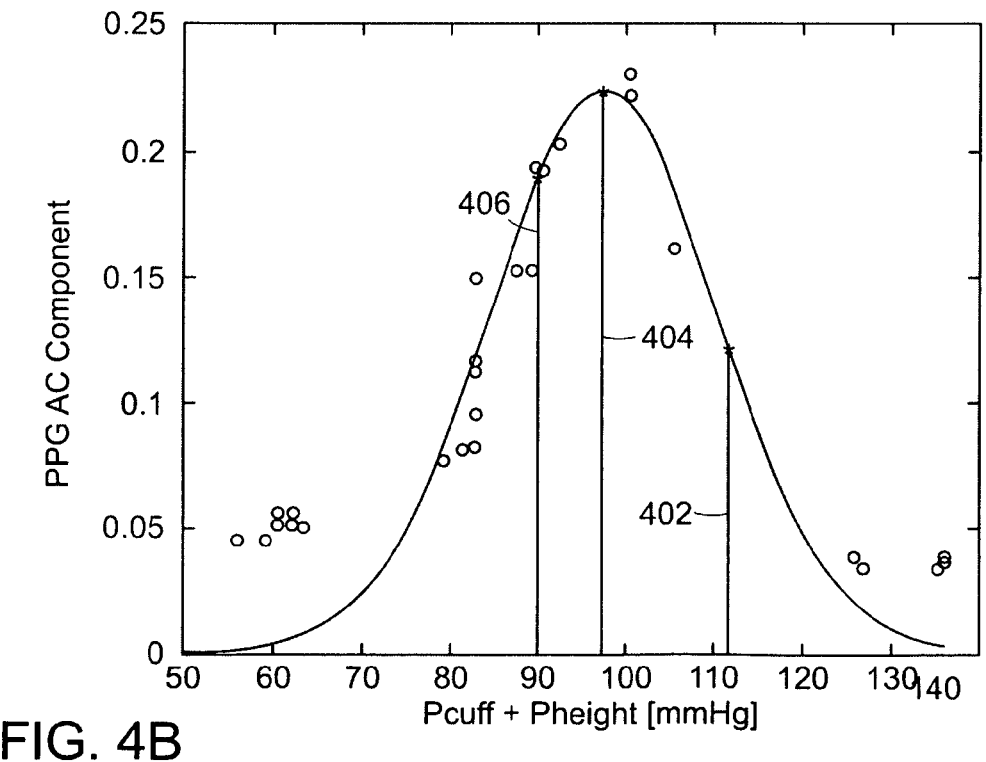
FIG. 4(b) is a plot of PPG amplitude vs. the sum of cuff pressure and hydrostatic pressure.

In accordance with embodiments of the invention, the diastolic and systolic blood pressures may also be identified from the non-linear calibration curve. FIG. 4(b) depicts the PPG amplitude component vs. cuff pressure plus the hydrostatic pressure. Systolic pressure 402 may be estimated as a point greater than the MAP 404 with an amplitude equal to a specified fraction, approximately half, of the maximum PPG amplitude. In accordance with preferred embodiments, a factor of 0.54 times the maximum PPG amplitude is employed. In other words, the maximum PPG amplitude is located on the nonlinear calibration curve. Next, the maximum PPG amplitude is multiplied by a factor of 0.54. The pressure along the x-axis corresponding to this new PPG amplitude is the estimated systolic pressure 402. The systolic pressure 402 will always be a higher pressure than the MAP (i.e. located to the right of the peak PPG amplitude value). Diastolic pressure 406 may be estimated using a process similar to systolic pressure 402 except that the multiplying factor is typically between 0.75-0.85. A preferred value is a factor of 0.84 times the maximum PPG amplitude. The systolic pressure 406 will always be less than the MAP 404. (i.e. located to the left of the peak PPG amplitude value).

Once the PPG-ABP calibration curve is established, there are several ways of measuring the ABP. In one embodiment, the PPG sensor unit pressure applied to the extremity is continuously or periodically varied so that the transmural pressure of the artery is near zero. The PPG sensor unit pressure is varied so that the PPG amplitude ($\bar{y}_{AC\_PPG}$) is similar to the peak PPG amplitude achieved during calibration (which was the point of zero transmural pressure). According to Eqn. (1), at zero transmural pressure, the ABP is equal to the value of the PPG sensor unit pressure plus the hydrostatic pressure. The value of the hydrostatic pressure can be found from the following equation:

$$P_{height} = -\rho \cdot g \cdot h \qquad (4)$$

wherein, $\rho$ is the density of the blood, g is the acceleration of gravity, and h is the height offset of the measurement site relative to the proximal aorta. Thus, with the known PPG sensor unit pressure and hydrostatic pressure the ABP can be found.

Figure 4C:
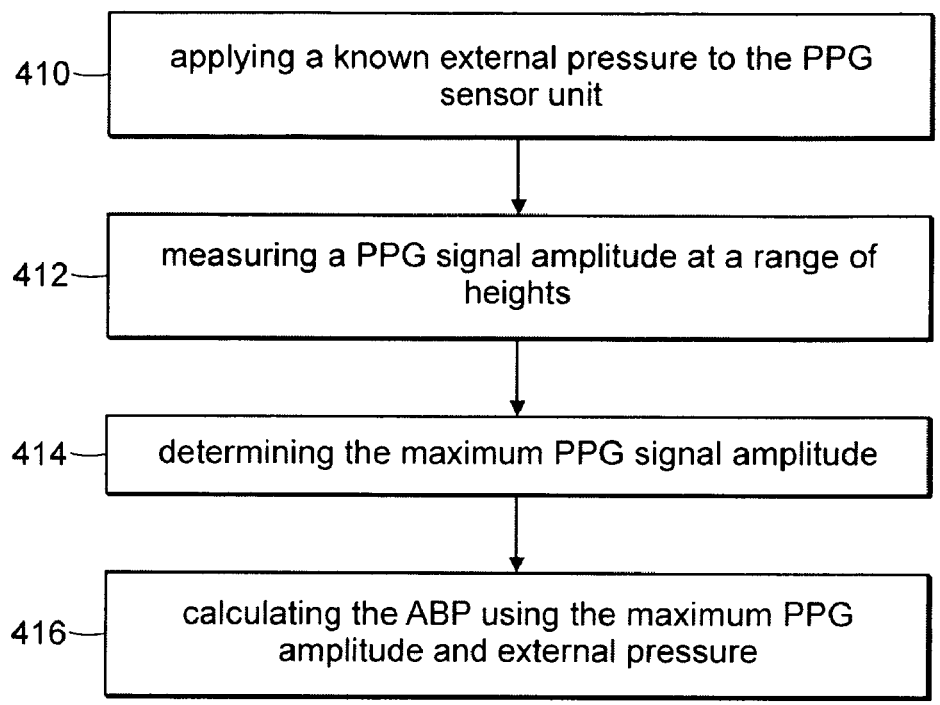
FIG. 4(c) depicts a block diagram for a method of measuring an arterial blood pressure, in accordance with an embodiment of the present invention.

In another embodiment, a constant PPG sensor unit pressure is applied to the extremity. Usually this PPG sensor unit pressure is near, or less than, the pressure applied during a previous calibration or measurement. Instead of varying the PPG sensor unit pressure applied to the extremity, the hydrostatic pressure is modulated by changing the height of the extremity. FIG. 4(c) depicts a method for measuring ABP using hydrostatic pressure 408. A PPG sensor unit pressure is applied to the extremity 410. In this embodiment the PPG sensor unit pressure is constant, however, in other embodiments the PPG sensor unit pressure may be modulated. Next, the extremity and the sensor are raised to a plurality of heights and the PPG amplitude is measured at each of the heights 412. In a preferred embodiment, the PPG amplitude is measured at a range of heights proximal the point where the transmural pressure is zero (transmural height). Once the PPG signal amplitudes are measured the peak PPG amplitude is determined 414. Like the calibration method above, spurious data points and oscillations between beats of the heart may be removed from the peak plethysmographic signal amplitude. If the PPG signal has a peak at the transmural height, then the ABP is equal to the previously calibrated MAP. However, if the peak PPG signal is at a different height, then the ABP is equal to the constant external pressure applied to the extremity plus the hydrostatic pressure, which can be found by solving Eqn. 4 with the new height 416.

In certain embodiments of the invention, the measurement itself can recalibrate the PPG-ABP relationship. Once the new height is found, it becomes the new transmural height. Also, once the new ABP is found, it becomes the new MAP. The next time a measurement is taken, the extremity is raised to the new transmural height and the PPG signal is checked against the maximum PPG amplitude of the new MAP. In other embodiments of the invention, instead of simply replacing the values, the different MAPs and transmural heights can be averaged.

Another way to measure ABP involves varying both the height and the external pressure applied to the extremity. In such an embodiment the extremity is raised to the transmural height. Then the external pressure applied to the extremity is modulated. If the modulation of external pressure does not result in an increase in the PPG signal amplitude then the ABP is equal to the MAP. If the modulation results in a peak amplitude at a different external pressure then the constant external pressure from the calibration, the ABP is the new external pressure plus the hydrostatic pressure at the new height.

A similar protocol can be used for calibration of the PPG-ABP curve. Instead of varying only the hydrostatic pressure, an external pressure can be applied which is anticipated to yield the maximum-amplitude PPG signal. In such an embodiment, there is no need to change the height of the extremity in small increments. The extremity can be moved to only two to three heights. For example, one height below the heart and one height above the heart, which is sufficient to confirm that the initial external pressure did produce the maximum PPG amplitude at the initial height level. The external pressure can be modulated at only two heights and the trasmural pressure located.[3]

It is important to note that the following apply equally to both PPG-ABP curve calibration and measurement. Both the PPG-ABP calibration curve and blood pressure measurements may be updated in real time based upon one or more of the following considerations:

(a) trends in time of an individual's prior calibration curves, (b) ancillary physiologic information that is obtained from:
  (i) motion sensors;
  (ii) temperature sensors;
  (iii) height data; and
  (iv) features in the PPG signal itself such as lower frequency oscillations that reflect the physiologic state of the local tissue; or PPG waveform shape/heart rate information that reflects changes in the subject's overall hemodynamic state;

(c) partial calibrations of the PPG-ABP relationship, which, while not traversing a wide-range of pressures, can reveal the presence or absence of major changes in the PPG-ABP curve.

Additionally, in accordance with yet further embodiments of the present invention, recalibrations of the PPG-ABP relationship and measurements are performed at intervals that optimize the balance between ABP accuracy, which favors frequent recalibrations/measurement, and wearer comfort/energy efficiency, which favors infrequent calibrations. The same predictors discussed above in the context of real-time updating of the calibration, e.g. trends in the PPG-ABP curve, data from ancillary signals, and results of partial calibrations, may each be factored into a determination of an optimal frequency of calibration.

In alternate embodiment; feedback, such as visual, audio, or tactile cues, can be used to guide the patient to appropriate actions. The appropriate actions can include recalibrating the PPG-ABP relationship, changing the height of the sensor, or positioning an extremity in a certain position. For example, when a chime is sounded, the patient might be directed to place his/her hand directly over the heart. In such an embodiment, the ABP may not be continuously measured, but measured at those instances when the patient has been notified that the hand/arm should be in a specific position.

Calibration may also be provided, in accordance with alternate embodiments of the invention, using means other than the height based sensor, which is described as one example of the operation of embodiments of the invention. For example, calibration and measurement can be accomplished by an external cuff/probe/sensor actuator, such as a conducting polymer actuator (as described below), or a small motor, or any other mechanical actuation means. In accordance with alternate embodiments of the invention, an umbilical cord may be provided, which runs up the arm up to the level of the heart, for direct continuous hydrostatic pressure measurement The height based sensor advantageously employs incidental movements of the subjects arm for updating the calibration curve and taking measurements, and for checking whether the calibration curve, most recently obtained, appears preserved or whether recalibration is necessary.

In accordance with preferred embodiments of the invention, a check of calibration validity, and an update as appropriate, may occur when the hand is at rest at whatever height. However, calibration while the hand is in motion is also within the scope of the invention, as is the use of noise cancellation algorithms during the process.

The importance of the height sensor for estimating MAP/ABP is noted, because the height of the hand is preferably taken into consideration when estimating central MAP/ABP from a peripheral signal.

In a preferred operational mode, a lower cuff pressure, in the general range of 30 mmHg, is applied, representing an optimal balance of comfort to the wearer (by virtue of the low pressure) and near-imperceptibility while maintaining adequate and consistent signal quality. Additionally, release intervals may be provided as needed to prevent blood buildup in the tissue due to applied pressures exceeding venous collapse pressures.

2) Height Measurement

Figure 5:
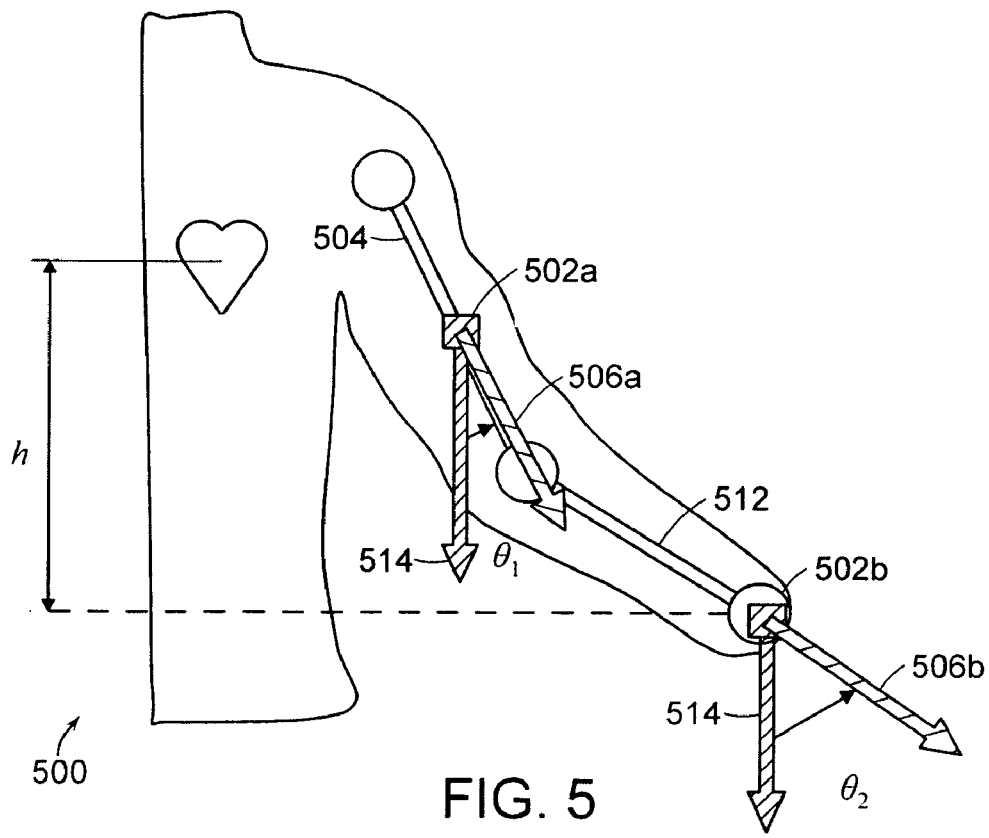
FIG. 5 shows two MEMS accelerometers, employed, for calculating the height of a sensor relative to the heart in accordance with an embodiment of the present invention.

In order to implement the algorithm described above, however, it is advantageous to measure the height, or vertical displacement, of the sensor relative to the heart. After all, the PPG output has been shown to vary with the height of the sensor, leading to an error in ABP estimation. Furthermore, the above algorithm exploits the dependence of ABP on height in order to perturb the input, the transmural pressure, for purposes of PPG calibration. FIG. 5. depicts a system 500 for height measurement. It is noted that the method and apparatus described herein may be applied to the measurement of the height of any fiduciary point on a limb.

Two single-axis accelerometers, preferably of micro-electro-mechanical system (MEMS) type, are disposed as follows:

A first accelerometer ACC1 502a is attached to the upper arm 504, with the axis 506a of the accelerometer aligned with the longitudinal direction of the upper arm; and A second accelerometer ACC2 502b is mounted on the blood pressure (BP) sensor, disposed at the wrist or the finger base, where the axis 506b of the accelerometer is aligned with the longitudinal direction of the forearm 512.

Although in this embodiment single axis accelerometers are used, in alternative embodiments, multi-axis accelerometers can be used.

As explained below, the output of each MEMS accelerometer 502a-b indicates the angle between the direction of gravity 514 and the direction of the accelerometer axis 506a-b. From ACC1, angle $\theta_1$, is obtained, that is, the angle between the direction of gravity 514 and that of the upper arm 504, and ACC2 gives $\theta_2$, that is, the angle between the gravity and that of the forearm 512, as shown in FIG. 5. The height of the heart relative to the PPG sensor, h, can be estimated as a function of these angles, $\theta_1$, and $\theta_2$.

Figure 6:
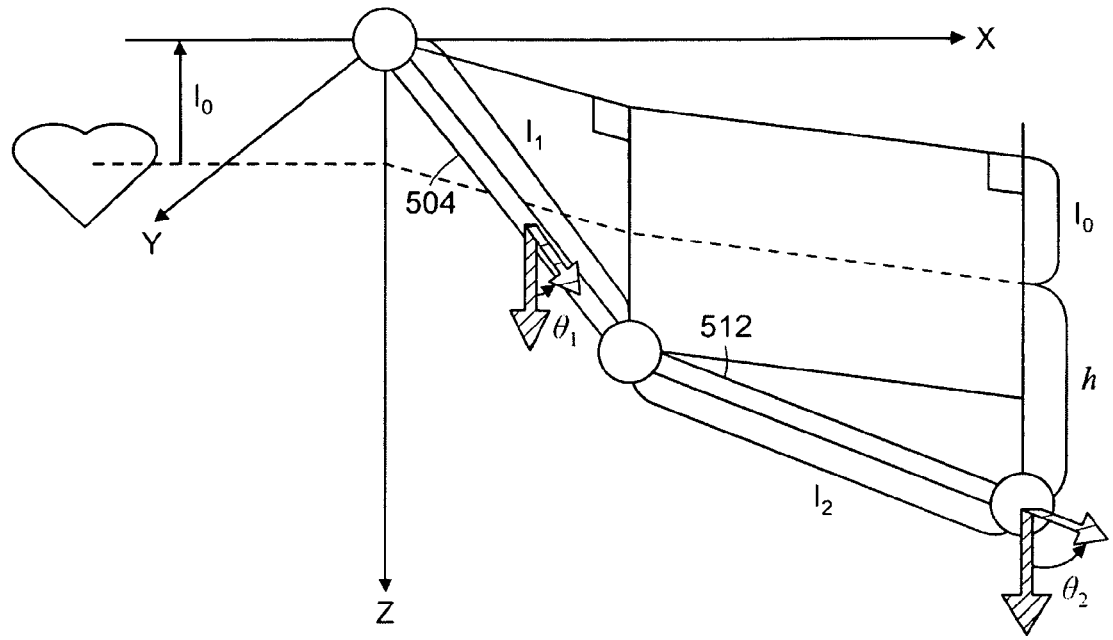
FIG. 6 shows derivation of the height of the ABP sensor relative to the heart, in accordance with an embodiment of the present invention.

FIG. 6 shows derivation of the height of the ABP sensor relative to the heart. $l_1$, and $l_2$ are the lengths of the upper arm 504 and the forearm 512, respectively, and $l_0$ is the height of the shoulder joint relative to the heart. The height of the heart relative to the PPG sensor is given by:

$$h = l_1 \cdot \cos\theta_1 + l_2 \cdot \cos\theta_2 - l_0.$$

The lengths $l_0$, $l_1$, and $l_2$ may be different from person to person depending on the body height as well as the location of the sensor. However, it can be assumed that they are proportional to the body height. Given the patient's body height, they can be approximated to average lengths $I_0$, $I_1$, and $I_2$ proportional to the body height. When the patient is lying, the third term in the above equation, i.e. $-l_0$, must be deleted.

Figure 7A:
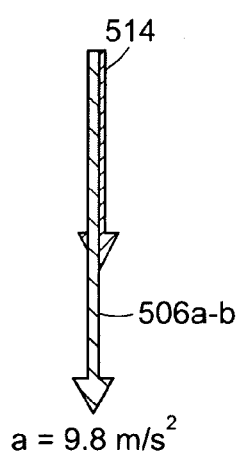
FIGS. 7(a)-(c) show derivation of relative limb angles based on accelerometer measurements, in accordance with an embodiment of the present invention.
Figure 7B:
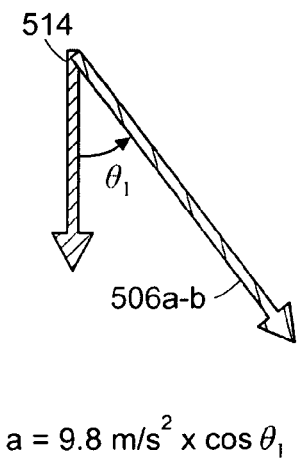
Figure 7C:
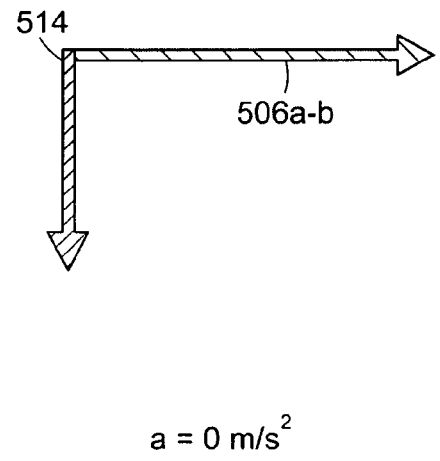

The cosine terms in the above equation can be obtained directly from the accelerometer readings as described with reference to FIGS. 7(a)-7(c). Those accelerometers, consisting of a mass-spring system, indicate the acceleration of gravity 514, i.e. 9.8 m/s$^2$, when directed to the vertical direction, as shown in FIG. 7(a). When the axis of the accelerometer 506a-b is kept horizontal, no acceleration is observed, as shown in FIG. 7(c). As the accelerometer axis 506a-b inclines, its output increases from 0 to 9.8 m/s$^2$, with an intermediary position depicted in FIG. 7(b). In principle the accelerometer reading is proportional to the cosine of the angle between the gravity vector and the accelerometer axis. Therefore, dividing the accelerometer output by 9.8 m/s$^2$ yields the cosine function value of the angles $\theta_1$, and $\theta_2$. Substitution of these cosine values into the above equation yields the height h.

This principle does not apply, when the arm is in motion. Before computing the height h, the height sensor must check if acceleration other than gravity is observed. To solve this problem, additional accelerometers or multi-axis accelerometers can be used instead of single axis accelerometers to sense arm motion in three dimensions. Another way to solve this problem is by using the accelerometers output signal along with time information. For example, the system may require a constant output from the accelerometers for a specified time period before the output is used to calculate the height. Thus, motion artifacts can be removed, better calibrating the accelerometer, and more accurately estimating the angles $\theta_1$, and $\theta_2$.

Also, time information and a temporal criterion can be used to ensure that the wearer is at rest for a certain amount of time before blood measurements are taken. Some blood pressure measurement regiments strive to track an individual's resting blood pressure. The time information and accelerometer output can be used to exclude measurements when the individual is not resting.

Other uses of the accelerometer data are also within the scope of the invention. For example, when the output signal from a single accelerometer indicates an acceleration of. 9.8 m/s$^2$, then the system can infer that the user's hand and sensor are at his side and thus, a fixed distance below his heart. Similarly, if the acceleration signal is 0.0 m/s$^2$, then the sensor is horizontal and the user's hand is approximately at the level of his heart. Addition of a time requirement (e.g., only make the preceding inference in the position persists for longer than 10 seconds) can help ensure that the preceding inferences are true, because, while it may be possible to briefly orient the hand horizontally but not have the entire arm horizontal, or hold the hand straight down without having the entire arm straight down, these unusual alternative positions are unlikely to be maintained for periods of more than a few seconds.

The calibration method 200 and height measurement system 500 of the present invention can normalize circulatory measurements to account for displacements of extremities. For example, a PPG sensor unit is calibrated using the calibration method 200 discussed above. Once calibration is complete, the subject moves his arm performing daily activities. As the subject's arm moves, the height of the sensor unit changes relative to his heart. The measurement system 500 acquires the height of the sensor unit relative to the subject's heart. From the previous calibration, the pressure change due to the current displacement of the extremity can be found. This pressure change is accounted for in the current pressure measurement.

3) Automatic Sensor Registration

As discussed above, one of the major difficulties of wearable health monitoring for the home and field use is proper attachment of the sensor to the skin, i.e. sensor registration. For the ABP sensor described previously, wherever the PPG sensor unit is to be placed near an artery, it may be difficult for the patient to find the right location of the artery and place the sensor. The following automatic registration algorithm and sensor design allow the for optimal response of the sensor unit wherever it may be placed on the finger base 802. Furthermore, the cuff pressure is automatically accommodated so that consistent and unified PPG signals may be obtained every time the patient puts on and takes off the sensor.

Further, methods in accordance with embodiments of the present invention may advantageously provide for long-term ambulatory measurement of arterial blood pressure (ABP) for home and field use, and provide for attachment of the sensor by average patients without supervision of clinicians.

Figure 8:
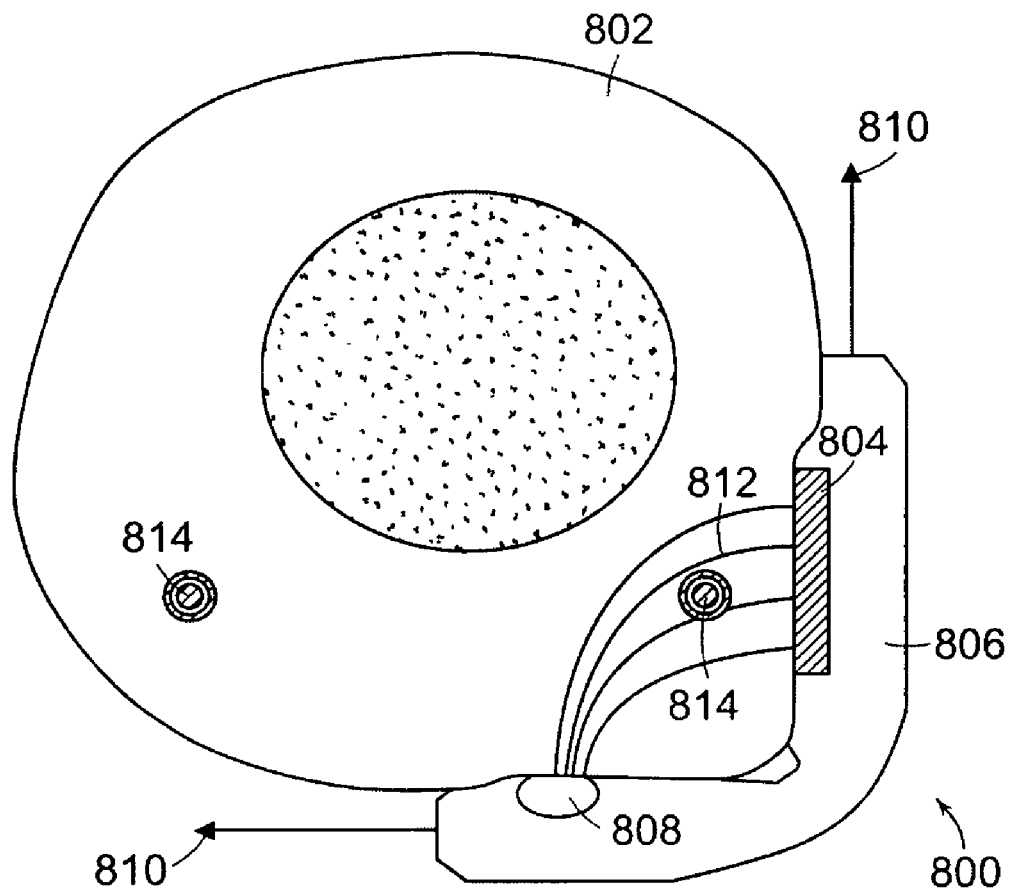
FIG. 8 is a cross-section of a PPG sensor unit in accordance with an embodiment of the present invention, as disposed about a finger base of a subject.

FIG. 8 shows a schematic of a PPG sensor unit 800 attached to a finger base 802. An array of photodetectors 804 is mounted on a sensor holder 806. The array of photodetectors employed in one embodiment is a linear array that includes 16 photodetectors, but other quantities are also suitable, as are arrays that contain more than a single row of photodetectors. Further, an LED 808 is mounted on the sensor holder 806. Although this embodiment contains an LED 808, other suitable light sources may be used. Both ends of the sensor holder 806 are pulled by a pair of actuators 810. The actuators may be the conducting polymer actuators described in the following section or any other means for applying external pressure to the finger base 802. As a result of the pulling force, the actuators 810, the array of photodetectors 804, and the LED 808 are pressed against the skin with an appropriate pressure. FIG. 8 illustrates conceptual light paths 812 from the LED 808 to the array of photodetectors 804. Depending on the location of a digital artery 814, signals captured by the individual photodetectors in the array 804 are different. Some photodetectors along the light path 812 going through the artery may capture strong pulsate signals, whereas other may contain weak or no signals. Although the exact location of the artery 814 is unknown, the photodetector having the largest signal may be identified by scanning all the signals coming out of the array 804.

Figure 9:
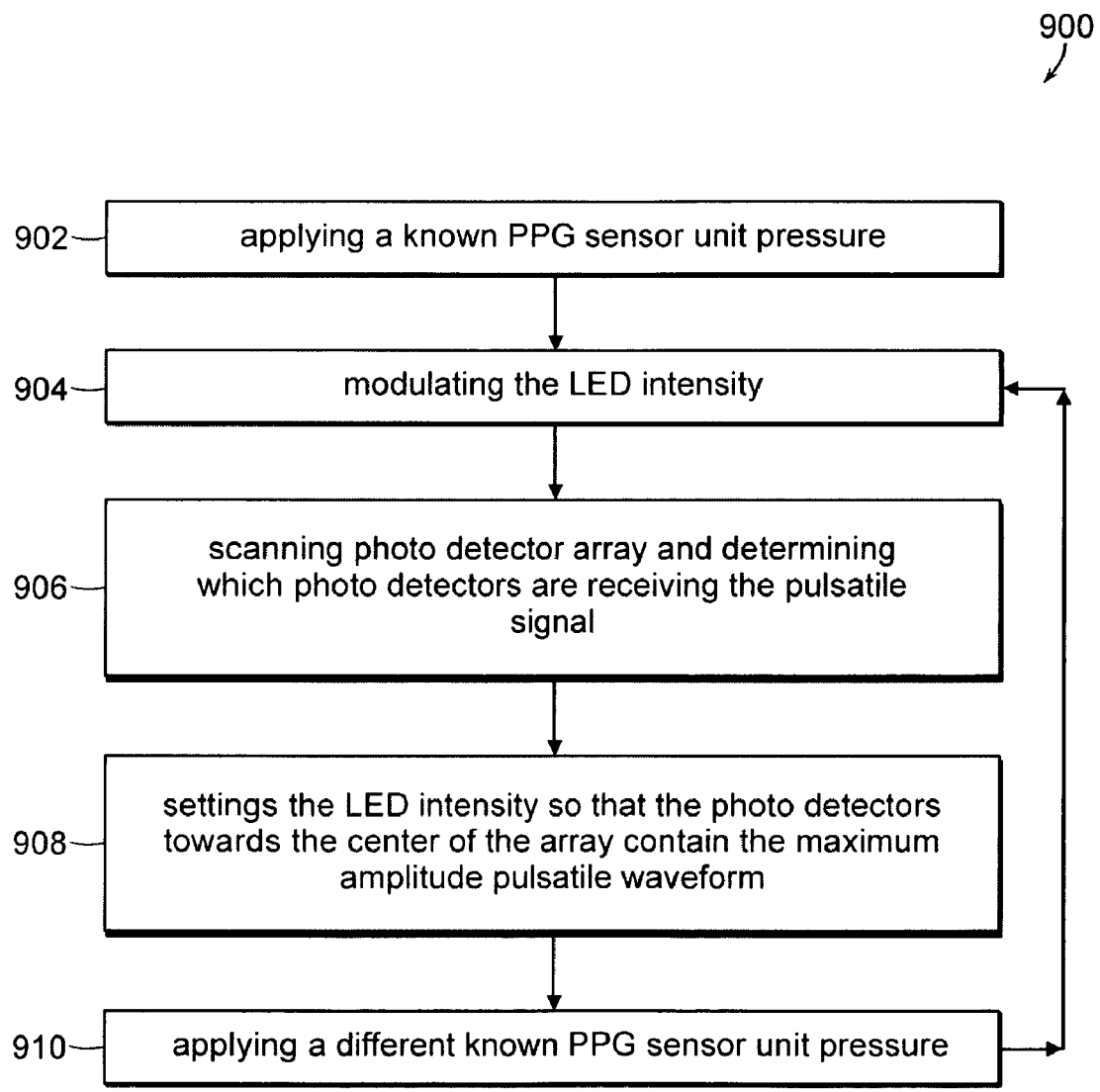
FIG. 9 depicts a block diagram for a method of sensor registration for optimizing response of a sensor unit, in accordance with an embodiment of the present invention.

During the scanning of the photodetector array 804, two other variables are varied: LED intensity and the PPG sensor unit pressure. Combining the LED intensity, the PPG sensor unit pressure, and array scan, a three-dimensional search of finding the best signal is performed. FIG. 9 illustrates a process for finding the best pulsatile signal 900. First, the PPG sensor unit 800 is positioned on the finger base 802. Next, the PPG sensor unit pressure applied to the finger base 802 is set to a low pressure of approximately 30 mmHg 902. Then, the LED intensity is slowly increased from a low level (<1 mA) to a high level (15 mA) 904 and the photodetector outputs are scanned to determine which photodetectors of the array 804 contain the pulsatile signal as the intensity is increased 906.

Ambient light may corrupt the signal received at the array of photodetectors 804. This problem is solved by separating ambient light from the pulsatile signal on the basis of the differential response among detectors of the array, or by synchronous detection based on the known frequency and/or phase of the source. While the DC intensity of the LED is slowly increased, a known periodic (AC—sinusoidal, for example) high frequency (in comparison to the pulse, referring, in preferred embodiments to frequencies above 1 kHz) intensity change is superimposed on the signal. The added periodic intensity change enables the separation of the light emitted from the LED 808 from the surrounding ambient light changes. Also, the added sinusoidal intensity enhances the positioning of the pulsatile waveforms within the photodetector array 804.

Once the intensity range has been scanned, the LED intensity is set so that the photodetectors towards the center of the array contain the maximum amplitude pulsatile waveform, if available 908. Next, the pressure is increased by 5 mmHg and the same scanning procedure is repeated 910. The procedure continues until a predefined pulsatile amplitude has been achieved or an external pressure of 50 mmHg has been applied to the finger of the patient. The sensor registration may be done continuously or at certain time intervals to correct for movement of the PPG sensor unit 800 around the finger base 802.

Since the optimal cuff pressure will vary based on the PPG signal obtained, the patient may move the sensor unit 800 around the finger base 802 in order to obtain better a PPG signal and thus, a more comfortable cuff pressure. In one embodiment of the invention, the PPG sensor unit 800 may provide the patient with audio, visual, or tactile cues in order to properly adjust the sensor unit 800 on the finger base 802. Based on the intensity of the pulsatile signals received by the array 804, the unit 800 will assist the patient in registering an optimal signal in a central photodetector. For example, if the intensity of the pulsatile signal is strongest on the right side of the photo detector array 804, the sensor unit 800 may ask the user to shift the unit in a clock-wise direction around the finger base 802 until the signal is centered on the array. The intelligent assistance of the sensor unit 800 helps ensure that an optimal signal is achieved and that a comfortable cuff pressure is achieved. Moreover, the sensor also advantageously ensures that the component of the device that applies external pressure is properly located directly over the artery when, and only when, the optical signal is properly located (by dint of the relationship between the device's geometry, the geometry of the patient's skin/tissue/artery, and patterns of light-propagation through the patient's skin/tissue/artery.

The pressure sensor unit 800 is not limited to use on a finger base 802, the sensor unit of the present invention may be useful in optimizing a PPG signal on the wrist, ankle, or an other part of an extremity.

4) Compact Cuff using Conducting Polymer Actuators

One of the key components involved in the PPG-based ABP sensor described above is a pressure-controllable cuff. For patient comfort, such a cuff must be compact and lightweight.

Figure 10:
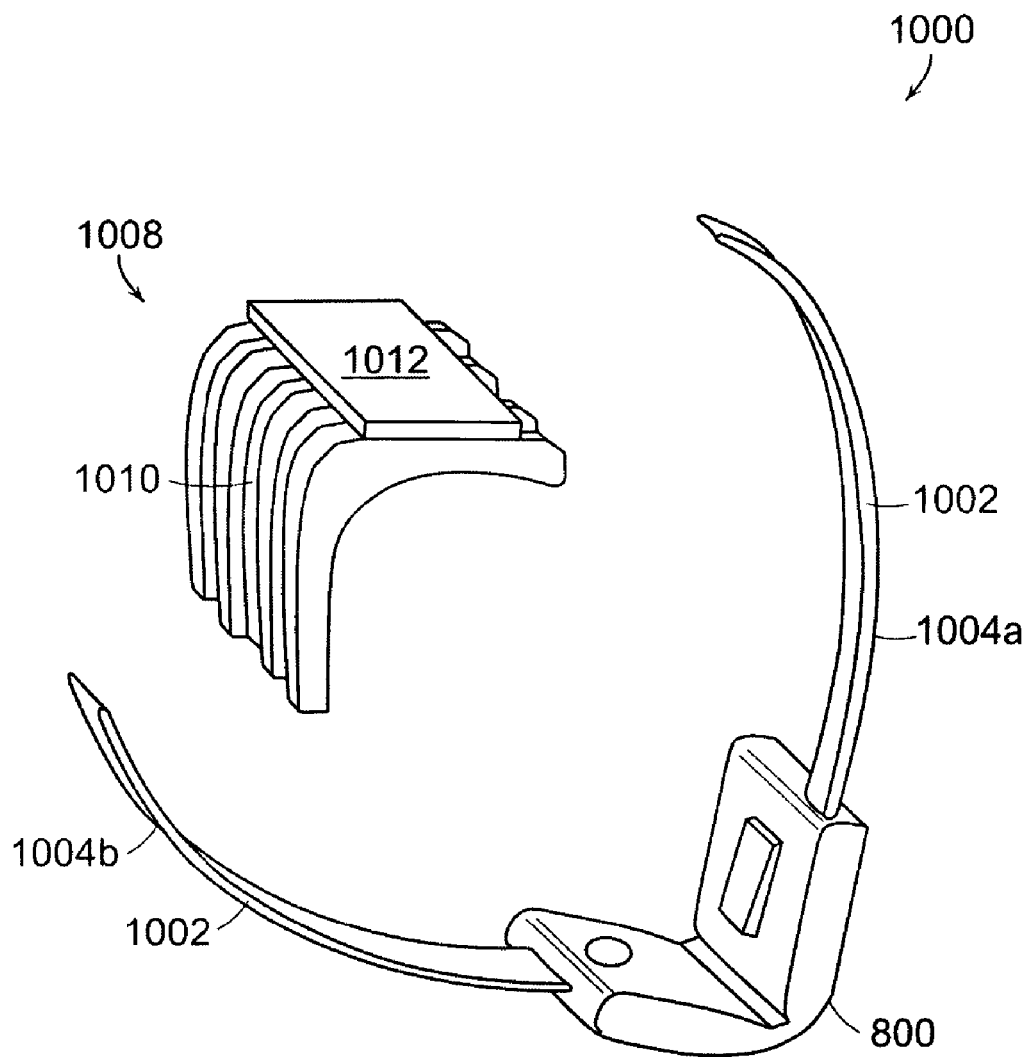
FIG. 10 shows an unassembled view of a wearable cuff employing conductive polymer actuators, in accordance with an embodiment of the present invention.

FIG. 10 shows an unassembled view of an embodiment of a compact wearable cuff 1000 using conducting polymer actuators 1002. Each conducting polymer actuator is encapsulated in a flexible tube filled with electrolyte. When electrically charged, the conducting polymers shrink or expand creating a strain of typically 5~15%. In accordance with one embodiment of the present invention, these conducting polymer actuators 1002 are used as active bands 1004a-b, which are wrapped around the finger or the wrist. As the conducting polymer actuators 1002 shrink, the pressure of the finger tissue under the PPG sensor unit 800 (PPG sensor unit pressure) increases.

The wearable cuff consists of four components: Active Band A 1004a, Active Band B 1004b, a sensor unit 800, and a band guide 1008 having grooves 1010 and a controller mount 1012. In one embodiment, the sensor unit 800 contains a PPG sensor, but the sensor unit may include other suitable means for measuring a plethysmograph signal.

Figure 11:
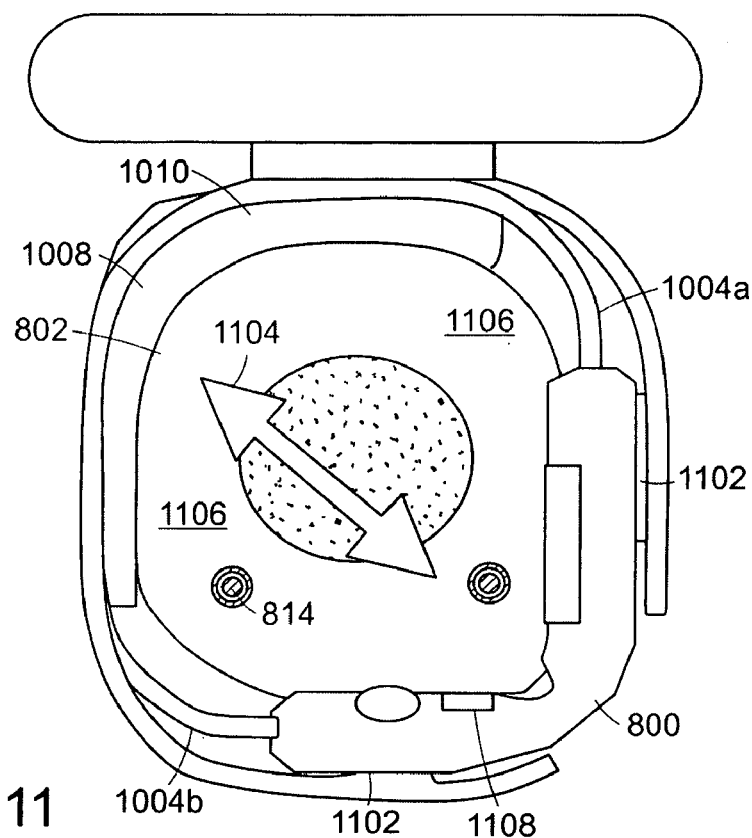
FIG. 11 shows a cross-section view of a wearable cuff employing conductive polymer actuators, in accordance with an embodiment of the present invention, as disposed about a finger base of a subject.

FIG. 11 shows an assembled view of the wearable cuff 1000. In this embodiment, Active Band A 1004a is connected to the upper end of the PPG sensor unit 800, is disposed in the grooves 1010 of the band guide 1008, is wrapped around the finger base 802, and is fixed to the PPG sensor unit again at the other end with a detachable tape 1102, such as Velcro. Depending on finger size, the active bands 1004a-b are secured at a different position on the PPG sensor unit 800. The detachable tape 1102 is long enough to cover different finger circumferences. Active Band B 1004b starts from the lower end of the PPG sensor unit 800, is disposed in the grooves 1010 of the band guide 1008, and is fixed to the PPG sensor unit 800 at the other end of the band with the detachable tape 1102. As both active bands 100a-b, shrink, the two rigid parts, i.e. the PPG sensor unit 800 and the band guide 1008, are pulled together, resulting in an increase in the pressure at the skin-side surface of the PPG sensor unit 800 (hereinafter PPG sensor unit pressure). The grooves 1010 of the band guide 1008 are of low friction so that the active bands 1004a-b can slide in the grooves smoothly.

Each active band 1004a-b makes an almost full turn, the total length of which measures 5~7 cm. The effective stroke of the active bands 1004a-b is approximately 6 mm, which is good enough to increase the cuff pressure to more than 200 mmHg, larger than the systolic pressure of average people. Since both the PPG sensor unit 800 and the band guide 1008 are rigid, the finger base 802 is compressed in a direction 1104 towards the PPG sensor unit. The wearable cuff 1000 generates a large pressure in the direction 1104a towards PPG sensor unit 800, while the cuff does not significantly increase pressure in surrounding tissue 1106. As a result, this wearable cuff 1000 configuration does not interfere with the blood flow at the arteries 814 in the surrounding tissue 1106, but effectively increases the PPG sensor unit pressure.

Figure 12:
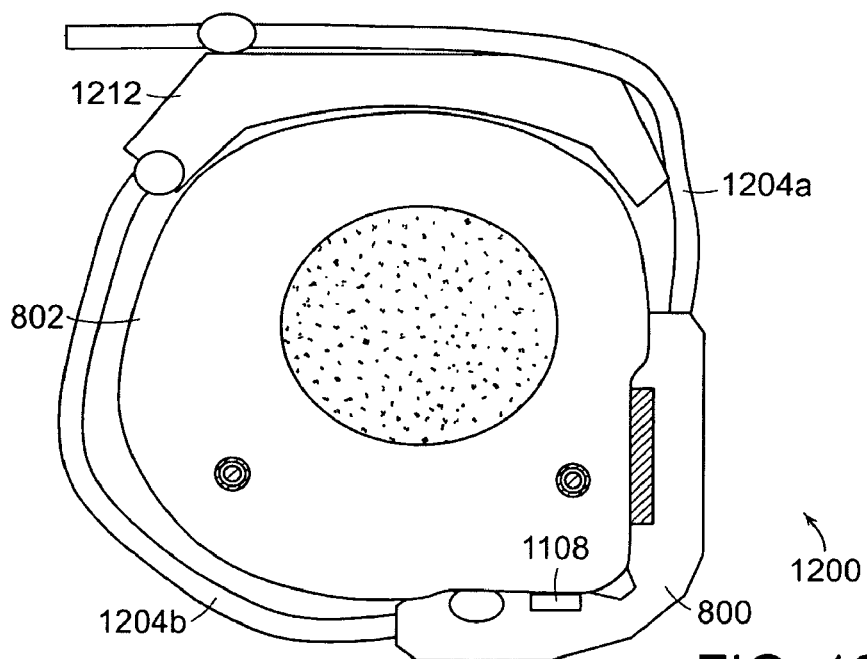
FIG. 12 is a cross-section of a PPG sensor unit, in accordance with another embodiment of the present invention, as disposed about a finger base of a subject.

FIG. 12 shows an alternative embodiment of the wearable cuff 1200. In this design each active band 1204a-b makes a half turn around the finger base 802. Active Band 1204a connects the upper end of the PPG sensor unit 800 to the right top corner of the controller mount 1212, while Active Band B 1206b connects the lower end of the PPG sensor unit 800 to the left bottom corner of the controller mount.

In another embodiment, the PPG sensor unit 800 may be surrounded by an outer casing, which decouples the sensor unit from interactions with the surrounding environment. The outer casing may protect the PPG sensor unit 800 from ambient light or outside physical forces.

Figure 13:
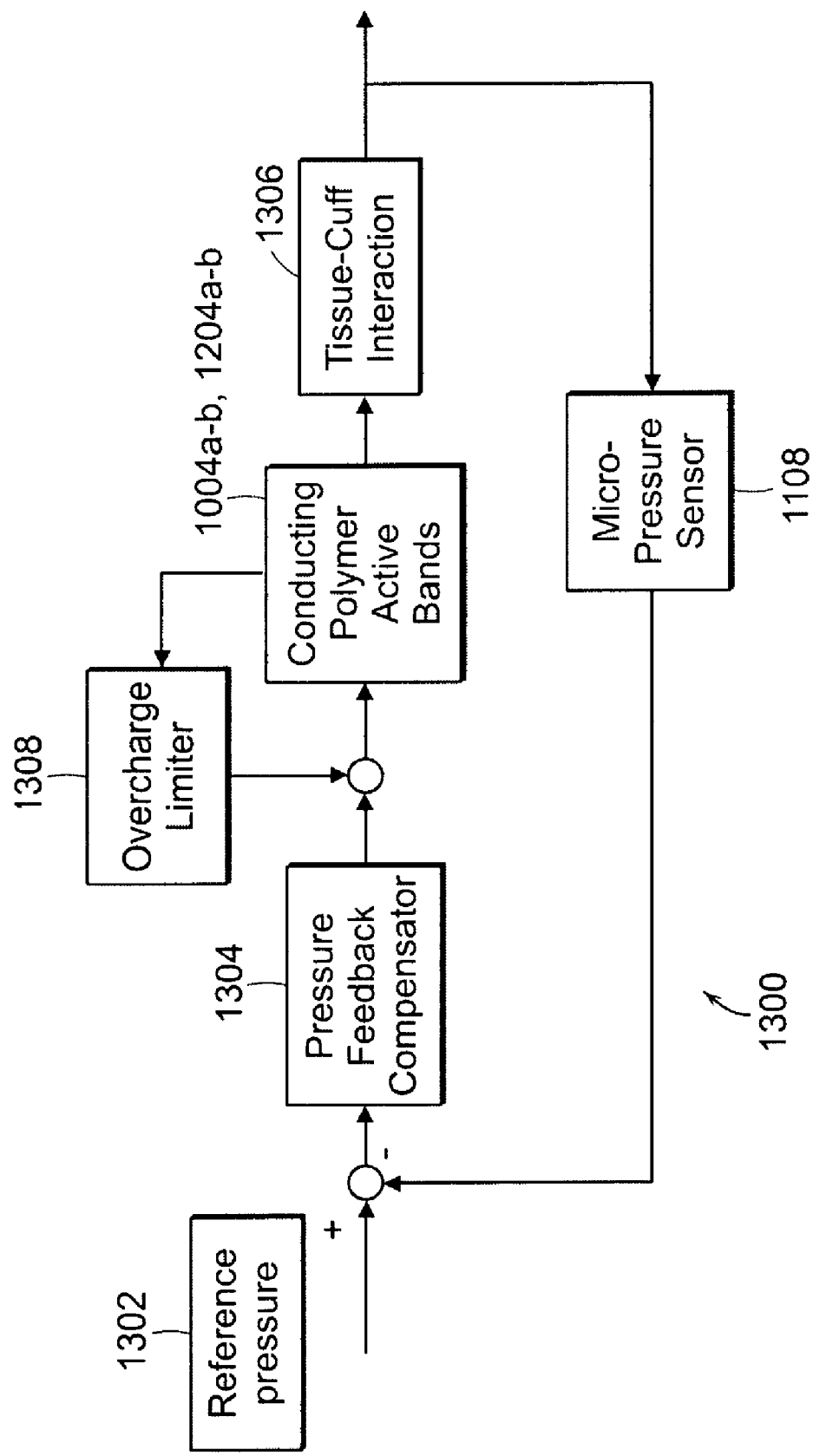
FIG. 13 is a block diagram of a pressure control system for applying voltage to conductive polymer active bands, in accordance with an embodiment of the present invention.

In the embodiments discussed above with reference to FIG. 11, or 12, the conducting polymer active bands 1004a-b, 1204a-b are pressure-controlled, using a micro-pressure sensor 1108 imbedded in the PPG sensor unit 800. One embodiment of the pressure-control system 1300 is depicted schematically in FIG. 13. A reference pressure 1302 is provided to a pressure feedback compensator 1304. The micro-pressure sensor 1108 provides a pressure feedback compensator 1304 with the actual PPG sensor unit pressure. Based on the actual PPG sensor unit pressure and the reference pressure 1302, the pressure feedback compensator 1304 adjusts the signal properties sent to the conducting polymer active bands 1004a-b, 1204a-b. According to the signal properties, the conducting polymer active bands in the wearable cuff 1000 apply pressure to the tissue of the patient 1306. The change in pressure is measured by the micro-pressure sensor 1108 and transmitted back to the pressure feedback compensator 1304 and again checked against the reference pressure 1302. Also, the system 1300 contains an overcharge limiter 1308 to ensure the pressure feedback compensator does not overload the conducting polymer active bands 1004a-b, 1204a-b.

5) Sensor Unit with a Protuberance

As discussed above, inflatable cuffs apply a known pressure to an extremity. The disadvantage with inflatable cuffs and other mechanisms for applying pressure is that they are bulky and difficult to miniaturize. Also, the mechanisms apply a large circumferential cuff pressure. The circumferential cuff pressure is uncomfortable for patients and may interfere with blood circulation. Moreover, when a mechanism for applying external pressure actuates it perturbs the positioning of the LED and photodetectors in relation to the finger base 802. This change of position will alter the light signals received at the photodetectors and create a less reliable PPG signal.

Figure 14:
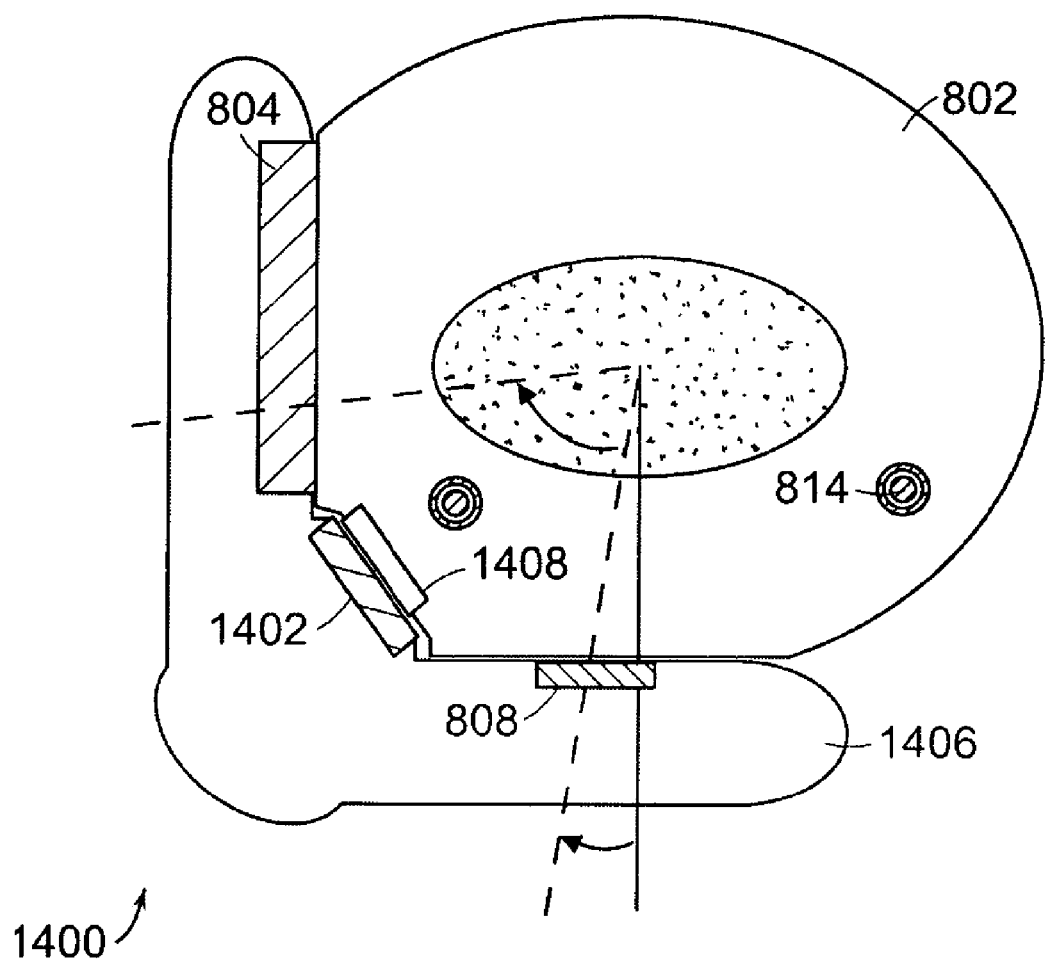
FIG. 14 shows a cross-section view of a PPG sensor unit with a protrusion, in accordance with an embodiment of the present invention, as disposed about a finger base of a subject.

FIG. 14 depicts a sensor unit 1400 having a sensor holder 1406 with a protuberance (or, protrusion) 1402 disposed on a finger base 802. Like the sensor units discussed above, the sensor unit 1400 in this embodiment also has an array of photodetectors 804 and a LED 808 mounted on the sensor holder 1406. The sensor holder 1406 may be built into a ring or band which holds the sensor holder 1406 on the finger base 802 and applies a constant pressure. The protrusion 1402 is solid and applies a known focal pressure to an artery 814. The protrusion, in accordance with the invention, does not induce applanation (flattening collapse) of the artery, but, rather, entails use of the sensor array described to insure that the small probe is properly located, and optic sensors on its flanks to measure oscillations in the face of different external pressures, using the techniques of oscillometry. The focal pressure can be measured by a pressure sensor 1408 located on or under the protrusion, or predicted from the design of the sensor unit 1400. For example, a tighter fit of the ring around the finger base 802 will force the sensor holder 1406 and protrusion 1402 into the finger base 802 and result in a greater focal pressure. If the circumference of the finger base 802 is known, the dimensions of the protrusion 1402 and fit of the band can be adjusted to apply a known focal pressure.

This configuration does not require a cuff or actuation mechanism to apply external pressure to an extremity. Since there is no need for an actuation means such as a pump or electric motor, the sensor unit 1400 is easy to miniaturize. A more reliable PPG signal is achieved because the actuation means does not shift the LED 808 and photodetectors 804 in relation to the finger base 802. Also, the protrusion 1402 applies a focal pressure to a localized area of the finger and does not interfere with circulation. The result is a more comfortable sensor unit.

Figure 15:
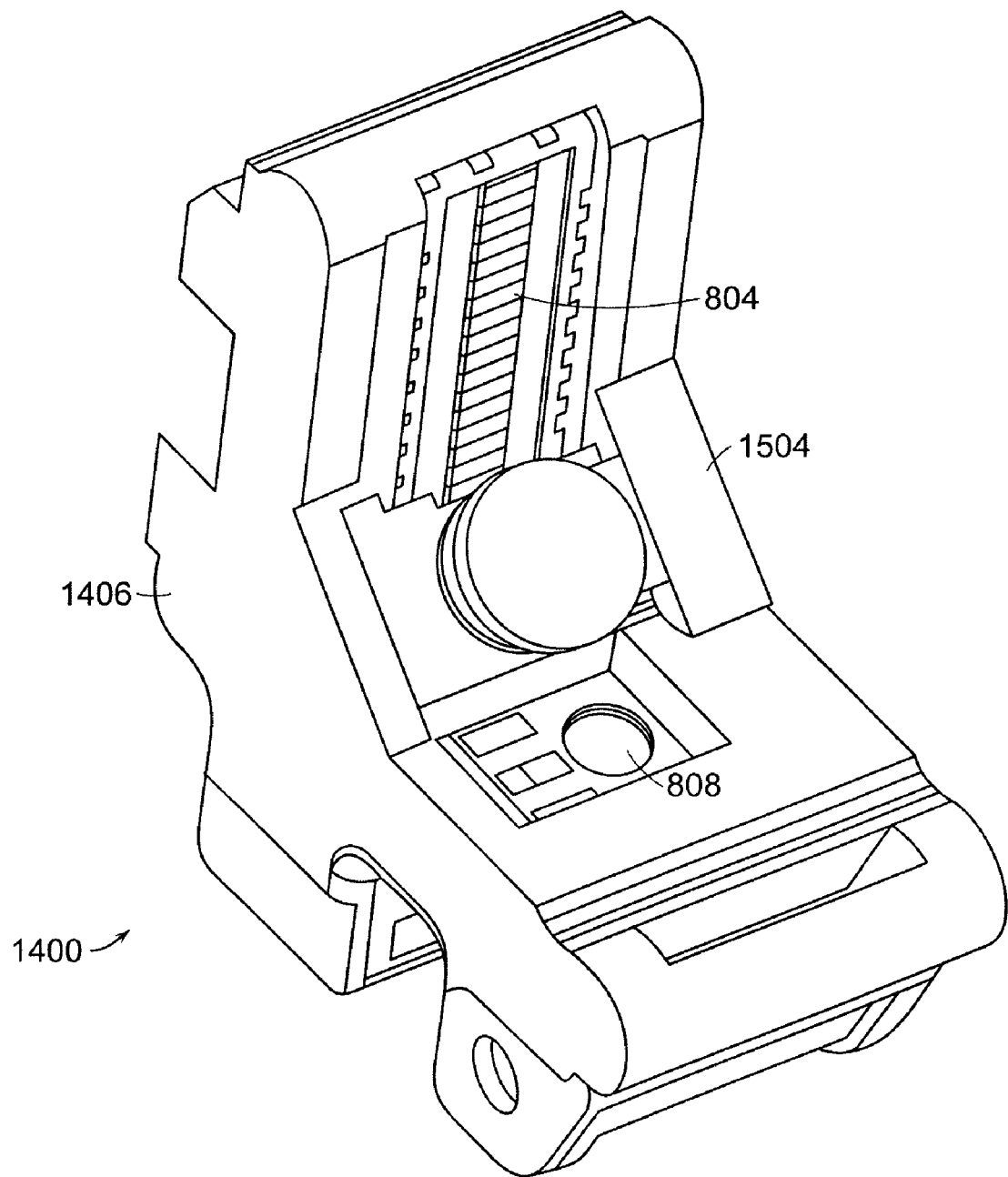
FIG. 15 is a perspective view of a PPG sensor unit, in accordance with one embodiment of the present invention.

FIG. 15 shows an embodiment of the sensor unit 1400 including the sensor holder 1406 with a cantilever assembly 1504. The cantilever assembly 1504 is positioned between a LED 808 and an array of photodetectors 804 at an angle of approximately 45 degrees relative to the palmar side of the fingerbase 802.

Figure 16:
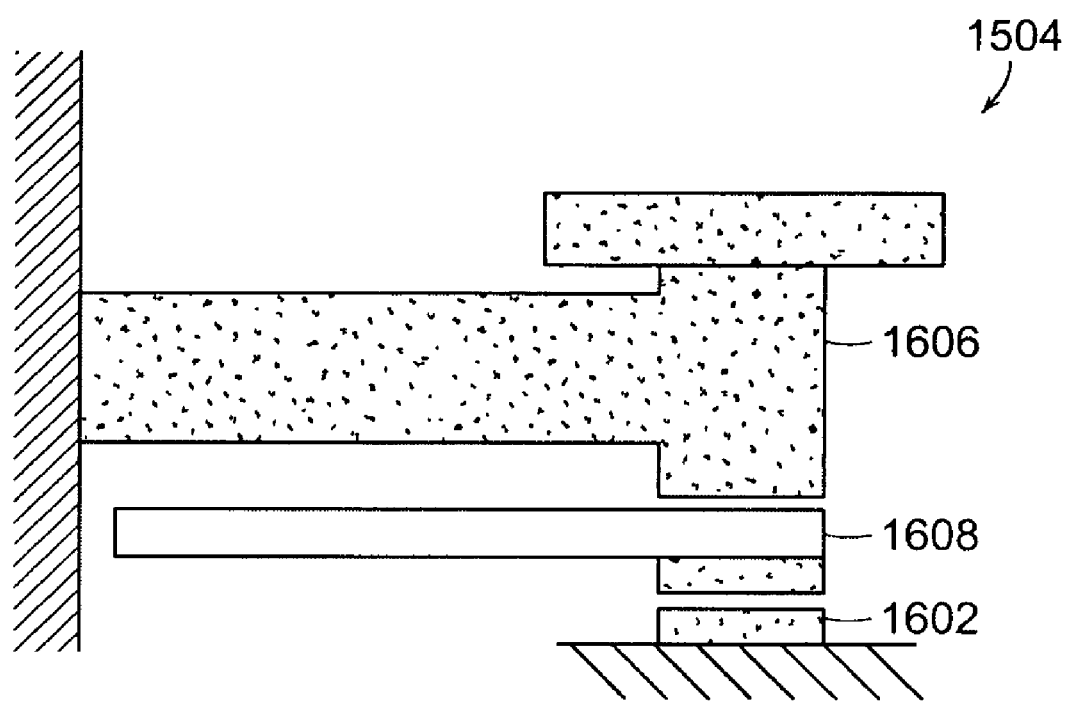
FIG. 16 shows a cross-section view of a cantilever assembly, in accordance with an embodiment of the present invention.

FIG. 16 is a cross-sectional view of the cantilever assembly 1504. The cantilever assembly 1504 contains a pressure sensor 1608 disposed between a cantilever 1606 and a small, rigid protrusion 1602. The pressure sensor 1608 may also be disposed under protrusion 1602, however, in this embodiment the diaphragm of the sensor 1608 is placed directly over the rigid protrusion 1602 and faces away from the surface of the finger base 802. The back side of the pressure sensor 1608 is in contact with the cantilever 1606 which protrudes from the surface of the sensor holder 1406 and presses directly into the medial-palmar surface of the fingerbase 802. The pressure sensor 1608 can be a low-profile pressure sensing element consisting of an encapsulated 10-psi (517-mmHg) strain gauge unit attached to a stainless steel diaphragm (Entran EPL-D02-/Z1). The pressure sensor 1608 measures approximately 5×10×1 mm. The output of the pressure sensor 1608 can be amplified and conditioned with a standard differential amplifier and $2^{nd}$ order Butterworth low-pass filter ($F_c$=1 Hz).

In a preferred embodiment the sensor unit 1400 is built into a ring which is disposed on the finger base 802. However, the senor unit can also be affixed to a band and disposed on the wrist. Further embodiments of the invention are built into a shirt sleeve, built into the neck of a collar shirt, built into a sock, or built into the leg band of elastic shorts.

In certain embodiments the sensor unit 1400 may be employed without an actuation mechanism for modulating external pressure. This embodiment would function by employing the hydrostatic pressure measurement method described in Sec. 1, wherein the external pressure applied is constant and the hydrostatic pressure is modulated.

Other embodiments of the sensor unit 1400 may be affixed to an actuation means such as an inflatable cuff, a DC motor, or the conductive polymer actuators of Sec. 4. Also, the protrusion 1402 itself can be inflatable or spring-loaded and capable of directly modulating the focal pressure. Such embodiments of the sensor holder with a protrusion are capable of employing methods of measuring that modulate external pressure applied to an extremity.

The described embodiments of the invention are intended to be merely exemplary and numerous variations and modifications will be apparent to those skilled in the art. In particular, hemodynamic parameters other than arterial blood pressure may be measured employing the techniques described herein and is within the scope of the present invention. All such variations and modifications are intended to be within the scope of the present invention as defined in the appended claims.

We claim:

1. A method for performing a circulatory measurement on an extremity of a subject, the method comprising:
    measuring a plethysmographic signal of a plethysmographic sensor disposed on the extremity of the subject at a plurality of heights of the sensor, relative to the heart of the subject, and at a plurality of externally applied pressures at each height of the sensor;
    while measuring the plethysmographic signal, using a solid protrusion to externally apply a focal pressure to the extremity of the subject, the focal pressure having a value that may vary;
    determining a relationship characterizing variation of the plethysmographic signal with the plurality of heights of the sensor and the plurality of externally applied pressures; and
    deriving an arterial blood pressure feature based on at least the relationship characterizing variation of the plethysmographic signal with the plurality of heights of the sensor and the plurality of externally applied pressures, and on an instantaneously measured plethysmographic signal and height of the sensor relative to the heart of the subject.

2. A method in accordance with claim 1, further comprising:
    modeling the relationship of a derived arterial pressure to the plethysmographic signal by fitting parameters of a specified functional relationship.

3. A method in accordance with claim 1, further comprising:
    modeling the relationship of a derived mean arterial pressure to a peak plethysmographic signal by fitting parameters of a specified functional relationship.

4. A method in accordance with claim 1, wherein the plethysmographic signal is a photoplethysmographic signal.

5. A method in accordance with claim 1, wherein the focal pressure is additionally varied by means of an inflatable cuff.

6. A method in accordance with claim 1, wherein the focal pressure is additionally varied by means of a band using a polymer actuator.

7. A method in accordance with claim 1, wherein measurement of a plurality of heights of the sensor is derived from at least one angular displacement of the extremity.

8. A method in accordance with claim 7, wherein the at least one angular displacement of the extremity is obtained by means of an accelerometer.

9. A method in accordance with claim 1, further comprising:
    removing spurious data points from the plethysmographic signal.

10. A method in accordance with claim 1, further comprising:
    removing oscillations between beats of the heart from the plethysmographic signal.

11. A method in accordance with claim 1, further comprising:
    deriving a systolic pressure by multiplying a peak plethysmographic signal by a specified factor.

12. A method in accordance with claim 11, wherein the factor is approximately 0.5.

13. A method in accordance with claim 1, further comprising:
    deriving a diastolic pressure by multiplying a peak plethysmographic signal by a specified factor.

14. A method in accordance with claim 13, wherein the factor is between 0.75 and 0.85.

15. A method in accordance with claim 1, wherein the arterial blood pressure feature is derived from the value of an externally applied pressure and the height at which a peak plethymographic signal is obtained.

16. An improved blood pressure measurement device of the type having a plethysmographic sensor disposed on an extremity of a subject capable of sensing a plurality of plethysmographic signals at a plurality of heights of the sensor relative to the heart of the subject, and at a plurality of externally applied pressures at each height of the sensor, the improvement comprising:
    a solid protrusion for externally applying a focal pressure to the extremity of the subject, the focal pressure having a value that may vary; and
    a processor receiving the plurality of plethysmographic signals from the sensor, the processor determining a relationship characterizing variation of the pelthymographic signal with the plurality of heights of the sensor and the plurality of externally applied pressures, deriving an arterial blood pressure feature based on at least the relationship characterizing variation of the plethysmographic signal with the plurality of heights of the sensor and the externally applied pressures, and on an instantaneously measured plethysmographic signal and height of the sensor relative to the heart of the subject.

17. A device in accordance with claim 16, wherein the processor models the relationship of a derived arterial pressure to plethysmographic signal by fitting parameters of a specified functional relationship.

18. A device in accordance with claim 16, wherein the focal pressure is additionally varied by means of an inflatable cuff.

19. A device in accordance with claim 16, wherein the focal pressure is additionally varied by means of a band using a polymer actuator.

20. A device in accordance with claim 16, wherein measurement of a plurality of heights of the sensor is derived from at least one angular displacement of an extremity.

21. A device in accordance with claim 16, wherein the processor contains a data filter for removing spurious data points from the plethysmographic signals.

22. A device in accordance with claim 16, wherein the processor is capable of deriving a systolic pressure by multiplying a peak plethysmographic signal by a factor.

23. A device in accordance with claim 22, wherein the factor is approximately 0.5.

24. A device in accordance with claim 16, wherein the processor is capable of deriving a diastolic pressure by multiplying a peak plethysmographic signal by a factor.

25. A device in accordance with claim 24, wherein the factor is between 0.75 and 0.85.

26. A device in accordance with claim 16, wherein the processor derives the arterial blood pressure feature from the value of an externally applied pressure and the height at which a peak plethymographic signal is obtained.

27. A method for performing a circulatory measurement on an extremity of a subject, the method comprising:
   measuring a plethysmographic signal of a plethysmographic sensor disposed on the extremity of the subject at a plurality of heights of the sensor, relative to the heart of the subject, and at a plurality of externally applied pressures at each height of the sensor;
   determining a relationship characterizing variation of the plethysmographic signal with the plurality of heights of the sensor and the plurality of externally applied pressures; and
   deriving an arterial blood pressure feature based on at least the relationship characterizing variation of the plethysmographic signal with the plurality of heights of the sensor and the plurality of externally applied pressures, and on an instantaneously measured plethysmographic signal and height of the sensor relative to the heart of the subject.

28. A method in accordance with claim 27, further comprising:
   modeling the relationship of a derived arterial pressure to the plethysmographic signal by fitting parameters of a specified functional relationship.

29. A method in accordance with claim 27, further comprising:
   modeling the relationship of a derived mean arterial pressure to a peak plethysmographic signal by fitting parameters of a specified functional relationship.

30. A method in accordance with claim 27, wherein the plethysmographic signal is a photoplethysmographic signal.

31. A method in accordance with claim 27, wherein external pressure is applied by means of an inflatable cuff.

32. A method in accordance with claim 27, wherein external the focal pressure is varied applied by means of a band using a polymer actuator.

33. A method in accordance with claim 27, wherein external pressure is applied by a sensor holder with a protrusion.

34. A method in accordance with claim 27, wherein measurement of a plurality of heights of the sensor is derived from at least one angular displacement of the extremity.

35. A method in accordance with claim 34, wherein the at least one angular displacement of the extremity is obtained by means of an accelerometer.

36. A method in accordance with claim 27, further comprising:
   removing spurious data points from the plethysmographic signal.

37. A method in accordance with claim 27, further comprising:
   removing oscillations between beats of the heart from the plethysmographic signal.

38. A method in accordance with claim 27, further comprising:
   deriving a systolic pressure by multiplying a peak plethysmographic signal by a specified factor.

39. A method in accordance with claim 38, wherein the factor is approximately 0.5.

40. A method in accordance with claim 27, further comprising:
   deriving a diastolic pressure by multiplying a peak plethysmographic signal by a specified factor.

41. A method in accordance with claim 40, wherein the factor is between 0.75 and 0.85.

42. A method in accordance with claim 27, wherein a mean arterial pressure is derived from a value of an externally applied pressure at which a peak plethysmographic signal amplitude is obtained and from the height at which a peak plethysmographic signal is obtained.

43. A method in accordance with claim 27, wherein the arterial blood pressure feature is derived from a value of an externally applied pressure and the height at which a peak plethymographic signal is obtained.

44. An improved blood pressure measurement device of the type having a plethysmographic sensor disposed on an extremity of a subject capable of sensing a plurality of plethysmographic signals at a plurality of heights of the sensor relative to the heart of the subject, and at a plurality of externally applied pressures at each height of the sensor, the improvement comprising:
   a processor receiving the plurality of plethysmographic signals from the sensor, the processor determining a relationship characterizing variation of the plethysmographic signal with the plurality of heights of the sensor and the plurality of externally applied pressures, and deriving an arterial blood pressure feature based on at least the relationship characterizing variation of the plethysmographic signal with the plurality of heights of the sensor and the externally applied pressures, and on an instantaneously measured plethysmographic signal and height of the sensor relative to the heart of the subject.

45. A device in accordance with claim 44, wherein the processor models the relationship of a derived arterial pressure to plethysmographic signal by fitting parameters of a specified functional relationship.

46. A device in accordance with claim 44, wherein external pressure is applied by means of an inflatable cuff.

47. A device in accordance with claim 44, wherein the focal pressure is varied by means of a band using a polymer actuator.

48. A device in accordance with claim 44, wherein the external pressure is applied by a sensor holder with a protrusion.

49. A device in accordance with claim 44, wherein measurement of a plurality of heights of the sensor is derived from at least one angular displacement of an extremity.

50. A device in accordance with claim 44, wherein the processor contains a data filter for removing spurious data points from the plethysmographic signals.

51. A device in accordance with claim 44, wherein the processor is capable of deriving a systolic pressure by multiplying a peak plethysmographic signal by a factor.

52. A device in accordance with claim 51, wherein the factor is approximately 0.5.

53. A device in accordance with claim 44, wherein the processor is capable of deriving a diastolic pressure by multiplying a peak plethysmographic signal by a factor.

54. A device in accordance with claim 53, wherein the factor is between 0.75 and 0.85.

55. A device in accordance with claim 44, wherein a mean arterial pressure is derived from a value of an externally applied pressure at which a peak plethysmographic signal is obtained and from the height at which a peak plethysmographic signal is obtained.

56. A device in accordance with claim 44, wherein the processor derives the arterial blood pressure feature from a value of an externally applied pressure and the height at which a peak plethymographic signal is obtained.

* * * * *

UNITED STATES PATENT AND TRADEMARK OFFICE
CERTIFICATE OF CORRECTION

PATENT NO. : 7,641,614 B2  Page 1 of 1
APPLICATION NO. : 11/508123
DATED : January 5, 2010
INVENTOR(S) : Asada et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 196 days.

Signed and Sealed this

Twenty-first Day of December, 2010

David J. Kappos
*Director of the United States Patent and Trademark Office*